(12) United States Patent
Lechmann et al.

(10) Patent No.: US 9,433,510 B2
(45) Date of Patent: Sep. 6, 2016

(54) EXPANDABLE INTERVERTEBRAL IMPLANT AND ASSOCIATED METHOD OF MANUFACTURING THE SAME

(71) Applicant: DePuy Synthes Products, Inc., Raynham, MA (US)

(72) Inventors: Beat Lechmann, Zuchwil (CH); Dominique Burkard, Gretzenbach (CH); Johann Fierlbeck, Salzburg (AT); Alfred Niederberger, Grenches (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/724,082

(22) Filed: May 28, 2015

(65) Prior Publication Data

US 2015/0257892 A1    Sep. 17, 2015

Related U.S. Application Data

(63) Continuation of application No. 14/032,231, filed on Sep. 20, 2013, which is a continuation of application No. 12/812,146, filed as application No. PCT/US2009/031567 on Jan. 21, 2009, now Pat. No. 8,551,173.

(60) Provisional application No. 61/021,778, filed on Jan. 17, 2008.

(51) Int. Cl.
*A61F 2/44* (2006.01)
*A61F 2/30* (2006.01)

(52) U.S. Cl.
CPC ............. *A61F 2/442* (2013.01); *A61F 2/3094* (2013.01); *A61F 2/44* (2013.01);

(Continued)

(58) Field of Classification Search
CPC .............................. A61F 2/442; A61F 2/3094
USPC ............................................ 623/17.11–17.16
See application file for complete search history.

(56) References Cited

U.S. PATENT DOCUMENTS

| | | |
|---|---|---|
| 4,349,921 A | 9/1982 | Kuntz |
| 4,863,476 A | 9/1989 | Shepperd |

(Continued)

FOREIGN PATENT DOCUMENTS

| | | |
|---|---|---|
| CN | 101909548 A | 12/2010 |
| DE | 4012622 | 7/1997 |

(Continued)

OTHER PUBLICATIONS

U.S. Appl. No. 61/675,975, filed Jul. 26, 2012, Lechmann et al.

(Continued)

*Primary Examiner* — Christopher Beccia
(74) *Attorney, Agent, or Firm* — Baker & Hostetler LLP

(57) ABSTRACT

An expandable intervertebral implant (10) includes superior (20) and inferior (30) bone contacting members and at least one vertical wire netting (50) interconnecting the superior and inferior bone contacting members. The superior and inferior bone contacting members include at least two bone contacting components interconnected via one or more lateral wire nettings such that the implant is vertically and laterally expandable in situ from a first insertion configuration to a second expanded configuration. The vertical and lateral wire netting are preferably constructed of a plurality of individual link members. The present invention also preferably relates to an associated method of manufacturing the intervertebral implant such that the intervertebral implant can be manufactured as an integral component or part.

17 Claims, 19 Drawing Sheets

(52) U.S. Cl.
CPC ............... *A61F 2002/3055* (2013.01); *A61F 2002/30556* (2013.01); *A61F 2002/30579* (2013.01); *A61F 2002/4475* (2013.01); *A61F 2250/0009* (2013.01)

(56) References Cited

U.S. PATENT DOCUMENTS

| | | |
|---|---|---|
| 5,059,193 A | 10/1991 | Kuslich |
| 5,290,312 A | 3/1994 | Kojimoto et al. |
| 5,344,252 A | 9/1994 | Kakimoto |
| 5,370,697 A | 12/1994 | Baumgartner |
| 5,390,683 A | 2/1995 | Pishardi |
| 5,443,514 A | 8/1995 | Steffee |
| 5,522,899 A | 6/1996 | Michelson |
| 5,534,029 A | 7/1996 | Shima |
| 5,554,191 A | 9/1996 | Lahille et al. |
| 5,609,635 A | 3/1997 | Michelson |
| 5,653,763 A | 8/1997 | Errico |
| 5,658,335 A | 8/1997 | Allen |
| 5,665,122 A | 9/1997 | Kambin |
| 5,697,977 A | 12/1997 | Pisharodi |
| 5,716,415 A | 2/1998 | Steffee |
| 5,772,661 A | 6/1998 | Michelson |
| 5,782,832 A | 7/1998 | Larsen et al. |
| 5,860,973 A | 1/1999 | Michelson |
| 5,865,848 A | 2/1999 | Baker |
| 5,888,224 A | 3/1999 | Beckers et al. |
| 5,893,889 A | 4/1999 | Harrington |
| 5,893,890 A | 4/1999 | Pisharodi |
| 5,980,522 A | 11/1999 | Koros et al. |
| 6,039,761 A | 3/2000 | Li |
| 6,045,579 A | 4/2000 | Hochshuler |
| 6,102,950 A | 8/2000 | Vaccaro |
| 6,106,557 A | 8/2000 | Robioneck et al. |
| 6,117,174 A | 9/2000 | Nolan |
| 6,127,597 A | 10/2000 | Beyar et al. |
| 6,129,763 A | 10/2000 | Chauvin et al. |
| 6,146,387 A | 11/2000 | Trott et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,193,757 B1 | 2/2001 | Foley et al. |
| 6,296,647 B1 | 10/2001 | Robioneck et al. |
| 6,302,914 B1 | 10/2001 | Michelson |
| 6,332,895 B1 | 12/2001 | Suddaby |
| 6,368,351 B1 | 4/2002 | Glenn |
| 6,375,682 B1 | 4/2002 | Fleischmann et al. |
| 6,387,130 B1 | 5/2002 | Stone |
| 6,409,766 B1 | 6/2002 | Brett |
| 6,419,705 B1 | 7/2002 | Erickson |
| 6,419,706 B1 | 7/2002 | Graf |
| 6,436,140 B1 | 8/2002 | Liu et al. |
| 6,454,806 B1 | 9/2002 | Cohen et al. |
| 6,454,807 B1 | 9/2002 | Jackson |
| 6,488,710 B2 | 12/2002 | Besselink |
| 6,527,804 B1 | 3/2003 | Gauchet et al. |
| 6,558,424 B2 | 5/2003 | Thalgott |
| 6,562,074 B2 | 5/2003 | Gerbec et al. |
| 6,582,468 B1 | 6/2003 | Gauchet |
| 6,610,094 B2 | 8/2003 | Husson |
| 6,641,614 B1 | 11/2003 | Wagner et al. |
| 6,648,917 B2 | 11/2003 | Gerbec et al. |
| 6,676,665 B2 | 1/2004 | Foley et al. |
| 6,706,070 B1 | 3/2004 | Wagner et al. |
| 6,719,796 B2 | 4/2004 | Cohen et al. |
| 6,723,126 B1 | 4/2004 | Berry |
| 6,733,532 B1 | 5/2004 | Gauchet et al. |
| 6,743,255 B2 | 6/2004 | Ferree |
| 6,805,714 B2 | 10/2004 | Sutcliffe |
| 6,855,167 B2 | 2/2005 | Shimp |
| 6,863,673 B2 | 3/2005 | Gerbec et al. |
| 6,893,464 B2 | 5/2005 | Kiester |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 7,018,412 B2 | 3/2006 | Ferreira et al. |
| 7,018,416 B2 | 3/2006 | Hanson et al. |
| 7,037,339 B2 | 5/2006 | Houfburg |
| 7,083,650 B2 | 8/2006 | Moskowitz et al. |
| 7,094,257 B2 | 8/2006 | Mujwid et al. |
| 7,211,112 B2 | 5/2007 | Baynham et |
| 7,217,293 B2 | 5/2007 | Branch |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,326,248 B2 | 2/2008 | Michelson |
| 7,503,933 B2 | 3/2009 | Michelson |
| 7,507,241 B2 | 3/2009 | Levy et al. |
| 7,569,074 B2 | 8/2009 | Eisermann et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,691,147 B2 | 4/2010 | Gutlin et al. |
| 7,703,727 B2 | 4/2010 | Selness |
| 7,722,612 B2 | 5/2010 | Sala et al. |
| 7,722,674 B1 | 5/2010 | Grotz |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,819,921 B2 | 10/2010 | Grotz |
| 7,824,445 B2 | 11/2010 | Biro et al. |
| 7,837,734 B2 | 11/2010 | Zucherman et al. |
| 7,846,206 B2 | 12/2010 | Oglaza et al. |
| 7,850,733 B2 | 12/2010 | Baynham et al. |
| 7,854,766 B2 | 12/2010 | Moskowitz et al. |
| 7,874,980 B2 | 1/2011 | Sonnenschein et al. |
| 7,879,098 B1 | 2/2011 | Simmons |
| 7,887,589 B2 | 2/2011 | Glenn et al. |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,177,812 B2 | 5/2012 | Sankaran |
| 8,192,495 B2 | 6/2012 | Simpson et al. |
| 8,221,501 B2 | 7/2012 | Eisermann et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 * | 10/2013 | Lechmann ............ A61F 2/3094 623/17.12 |
| 8,556,979 B2 | 10/2013 | Glerum et al. |

(56) References Cited

U.S. PATENT DOCUMENTS

| | | |
|---|---|---|
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 9,095,446 B2 | 8/2015 | Landry et al. |
| 9,095,447 B2 | 8/2015 | Barreiro et al. |
| 2002/0068976 A1 | 6/2002 | Jackson |
| 2002/0068977 A1 | 6/2002 | Jackson |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0165485 A1 | 7/2005 | Trieu |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0140207 A1 | 6/2008 | Olmos |
| 2008/0147193 A1 | 6/2008 | Matthis et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0179594 A1 | 7/2010 | Theofilos et al. |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |

(56) References Cited

U.S. PATENT DOCUMENTS

| | | |
|---|---|---|
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0185049 A1 | 7/2012 | Varela |
| 2012/0197403 A1 | 8/2012 | Merves |
| 2012/0226357 A1 | 9/2012 | Varela |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0045894 A1 | 2/2015 | Hawkins et al. |
| 2015/0094812 A1 | 4/2015 | Marden et al. |
| 2015/0094813 A1 | 4/2015 | Lechmann et al. |

FOREIGN PATENT DOCUMENTS

| | | |
|---|---|---|
| DE | 202008001079 | 3/2008 |
| EP | 1290985 | 3/2003 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2874814 | 3/2006 |
| JP | 2003-526457 | 9/2003 |
| JP | 2006-516456 | 7/2006 |
| JP | 2011-509766 A | 3/2011 |
| WO | WO 95/31158 | 11/1995 |
| WO | WO 97/00054 | 1/1997 |
| WO | WO 00/12033 | 3/2000 |
| WO | WO 00/74605 | 12/2000 |
| WO | WO 01/01895 | 1/2001 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/009107 | 1/2007 |
| WO | WO 2007/028098 | 3/2007 |
| WO | WO 2007/048012 | 4/2007 |
| WO | WO 2008/044057 | 4/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |

OTHER PUBLICATIONS

U.S. Appl. No. 14/685,358, filed Apr. 13, 2015, Marden et al.
U.S. Appl. No. 14/640,220, filed Mar. 6, 2015, Marden.
U.S. Appl. No. 14/685,402, filed Apr. 13, 2015, Cain.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).

* cited by examiner

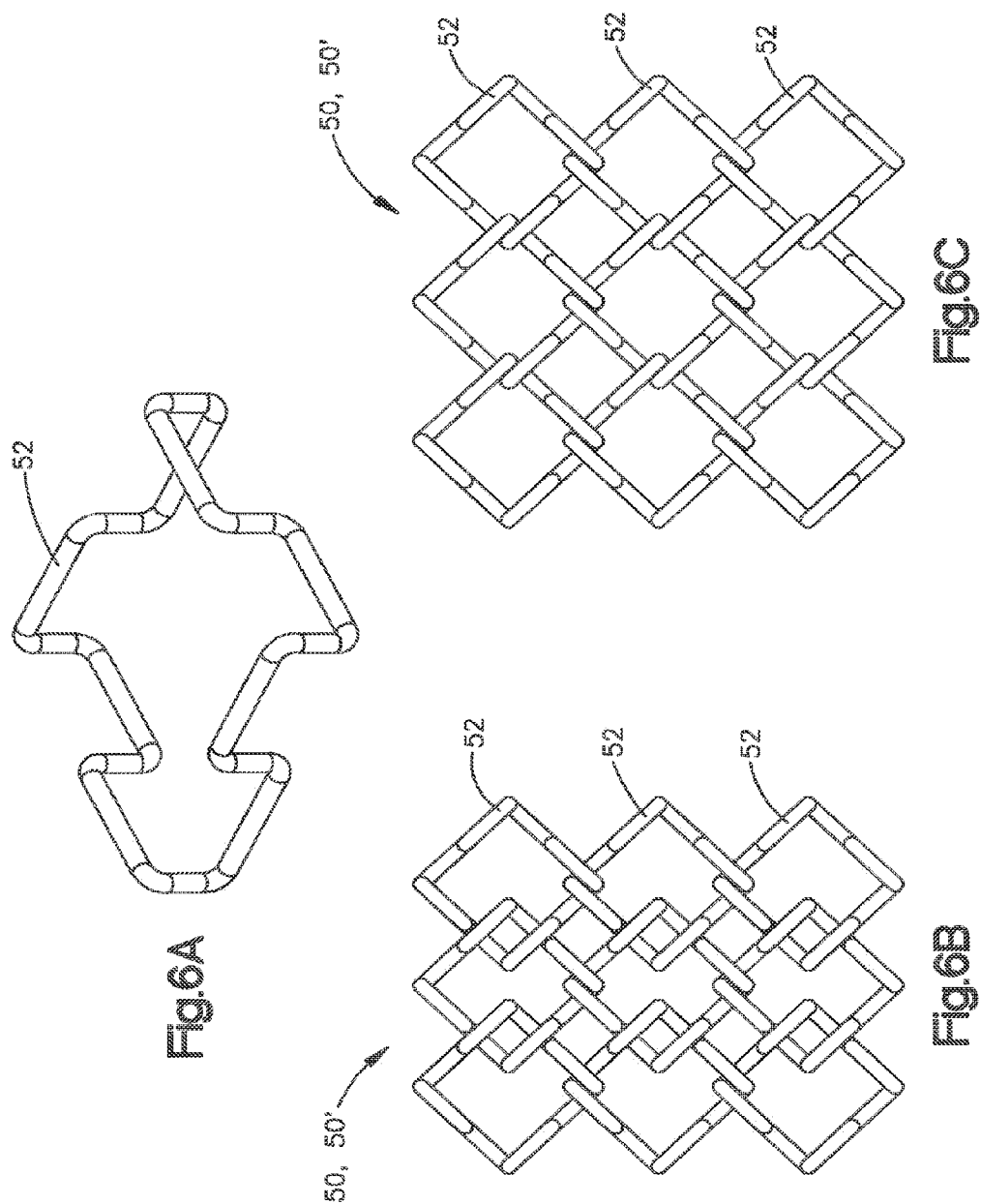

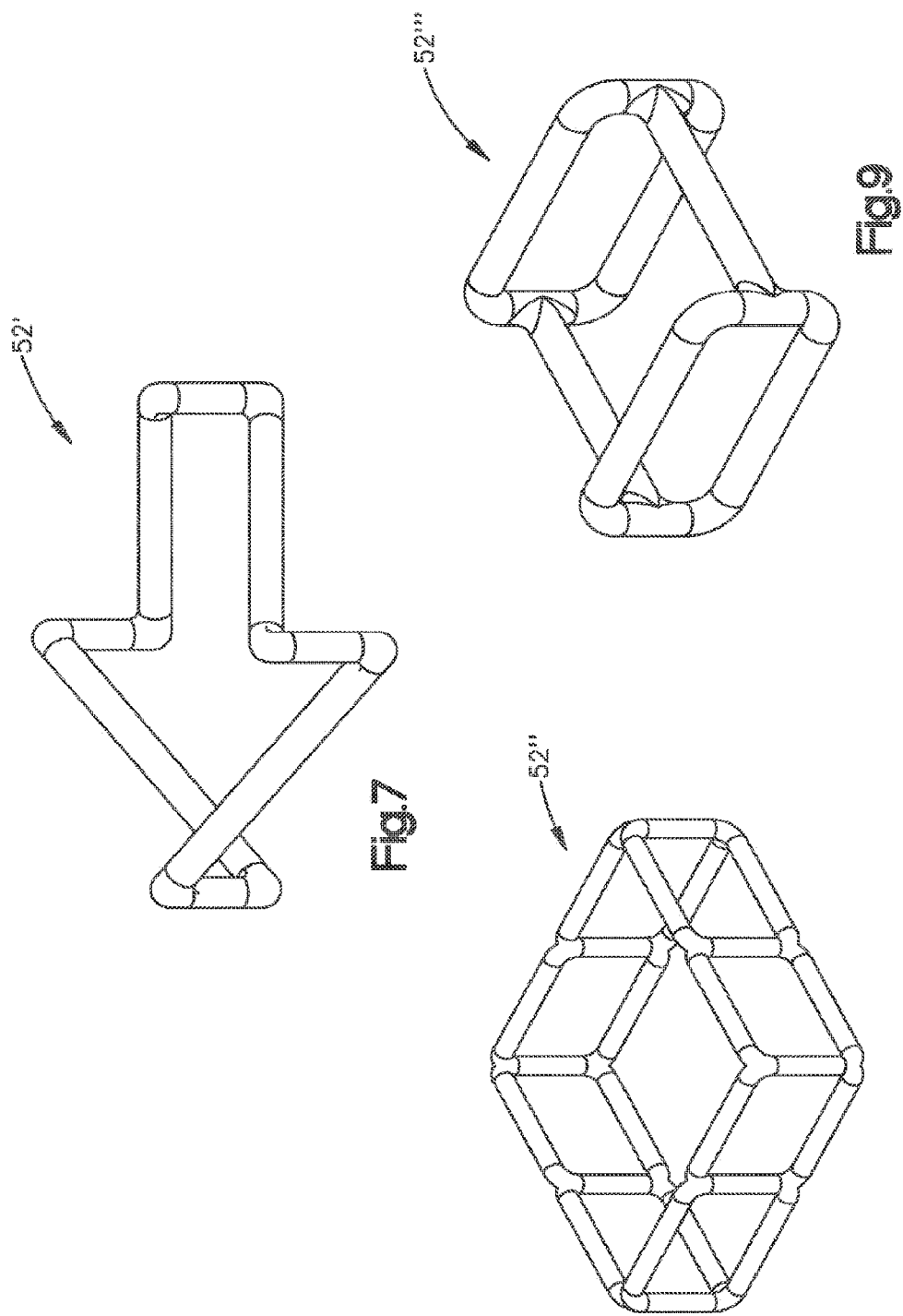

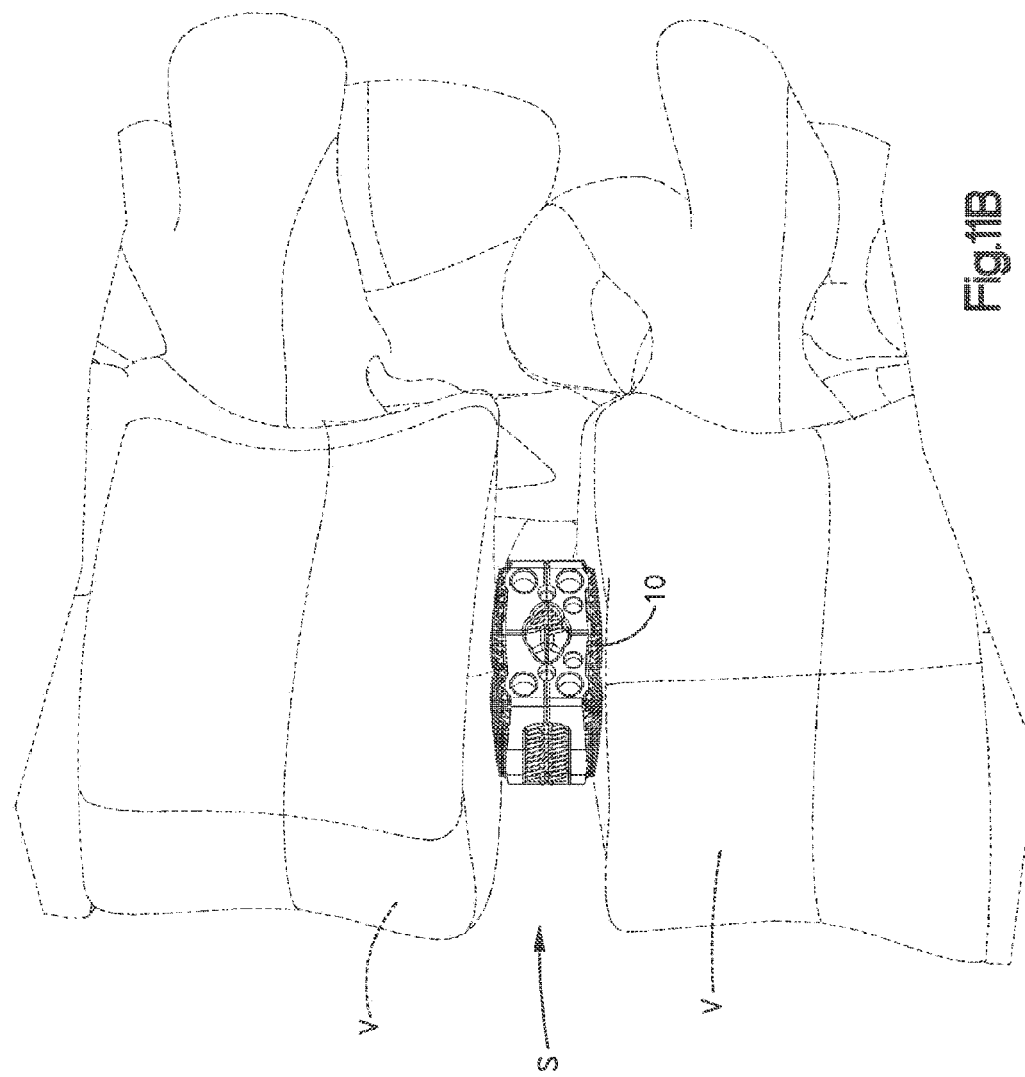

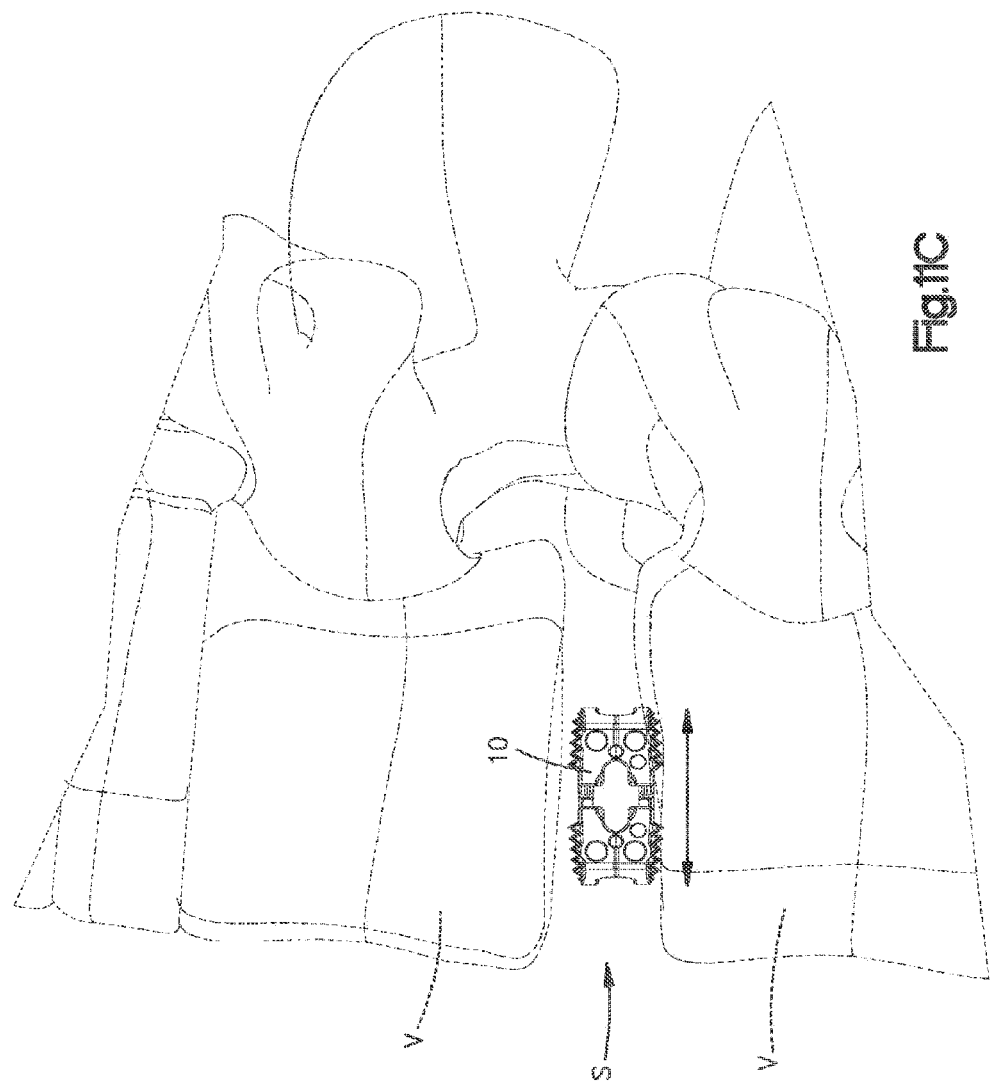

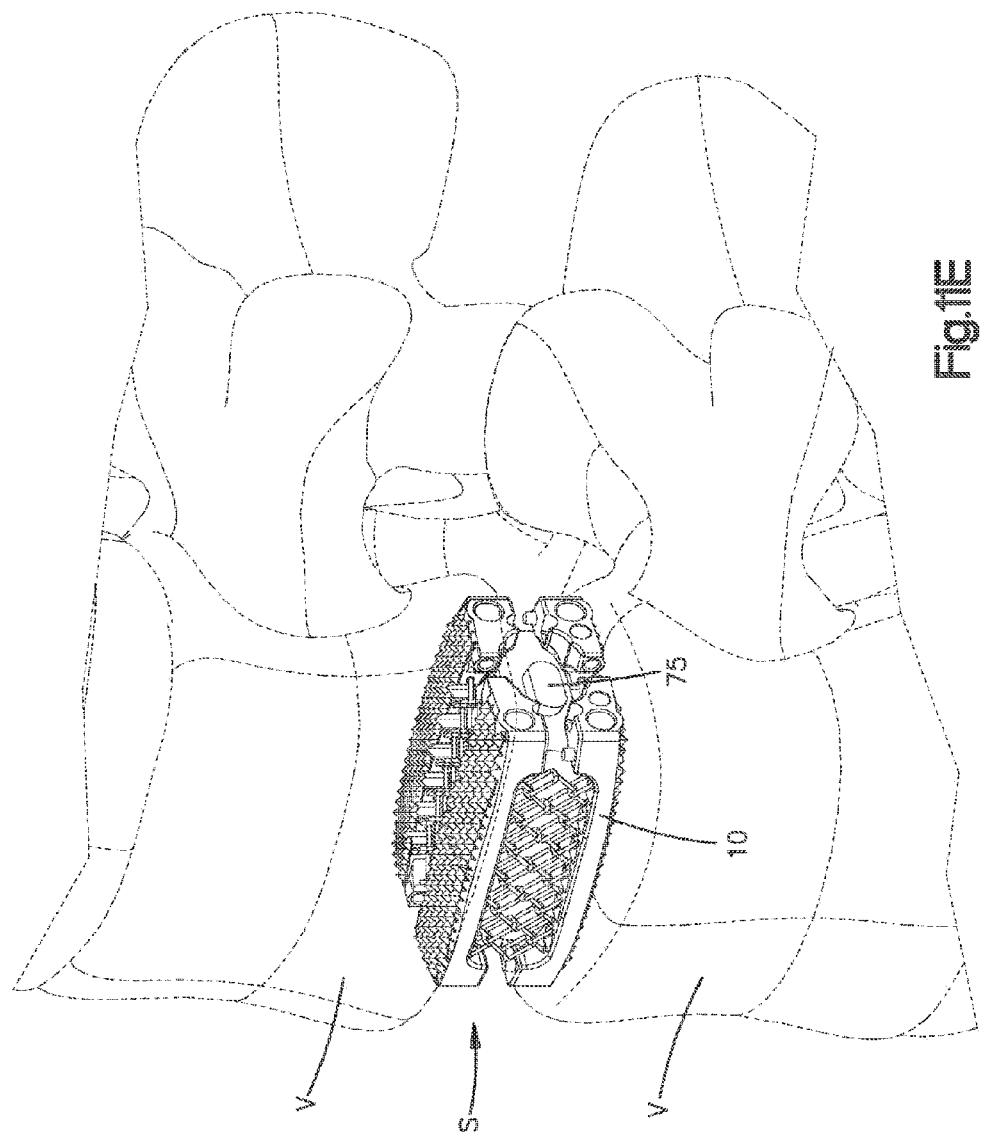

EXPANDABLE INTERVERTEBRAL IMPLANT AND ASSOCIATED METHOD OF MANUFACTURING THE SAME

CROSS REFERENCE TO RELATED APPLICATIONS

This application is a continuation of pending U.S. patent application Ser. No. 14/032,231 filed Sep. 20, 2013, which is a continuation of U.S. patent application Ser. No. 12/812,146, filed Jul. 8, 2010, which is a national stage application under 35 U.S.C. §371 of International Application No. PCT/US2009/031567, filed on Jan. 21, 2009, which claims the benefit of U.S. Provisional Application No. 61/021,778, filed on Jan. 17, 2008. The entire content of each aforementioned application is incorporated by reference herein for all purposes.

BACKGROUND

People, especially elderly people, may suffer from osteoporosis. One aspect of osteoporosis may be the partial or complete collapse of the bony structure of the spine, which in turn can cause loss of vertebral height, fracture of a vertebral disc, facet and nerve impingement, etc. Collapse of the spine often results in, for example, pain, reduction of lung function, unbalanced stature, etc. One treatment option may be a surgical procedure to re-align the vertebra (e.g., to re-establish balanced curvature of the spine as well as the intervertebral disc space).

Re-alignment of a spine including a damaged vertebra or disc may be accomplished by replacing the damaged vertebra, disc or portions thereof with an intervertebral implant. That is, an intervertebral implant may be inserted into the intervertebral disc space of two neighboring vertebral bodies or into the space created by removal of portions of or the entire vertebral body after removal of damaged portions of the spine. Preferably, the intervertebral implant restores the spine, as much as possible, to a natural state, i.e. to restore the original height of the intervertebral disc or the series of vertebra and, thus, the original distance between the two neighboring or adjacent vertebral bodies or vertebral bodies in various levels of the spine.

Typically implantation of one or more intervertebral implants is not part of a treatment procedure for osteoporosis. One reason for this may be that intervertebral implants are often designed with high structural stiffness. Osteoporotic bone is usually brittle, thus increasing the risk of breaking a vertebral endplate during a surgery or implantation of an implant and the endplates may have a uneven surface. For example, a stiff implant may impact a point or small area of an uneven surface of the osteoporotic bone, thereby creating a stress concentration and potentially damaging the bone. Therefore, the incorporation of an intervertebral implant in certain cases, is contra-indicated for patients with osteoporotic bone. Another reason for not incorporating an intervertebral implant may be that the insertion approach for implanting an intervertebral implant is difficult and risky, especially in elderly patients.

Alternatively, rather than implanting an intervertebral implant, a surgeon may elect to perform a Vertebralplasty and/or Cavitoplasty procedure on the patient's spine. In an exemplary method of performing a Vertebralplasty and/or Cavitoplasty procedure, a protective sleeve or cannula may be inserted into the patient's body, adjacent to the patient's spine. The spine may then be re-aligned if fractured or re-fractured. Next cement is inserted into the spine to replace lost bone and/or to limit future cracks. After the hardening of the cement, the treated section of the spine may be re-aligned and the patient may then return to his or her daily activity. In a Cavitoplasty procedure, a cavity may be formed in one or more of the vertebral bodies for receiving a portion of the cement.

It would be desirable to construct an intervertebral implant that is relatively simple to insert into a patient's spine at a relatively small size and which is able to expand to restore the original height of the removed spinal material or to a height desired by a surgeon. It would also be desirable to construct an intervertebral implant that is adaptable to uneven surfaces of an osteoporotic vertebral bone to limit stress concentrations when the implant is expanded and contacts or applies pressure to a patient's endplate.

SUMMARY

The present invention relates to an expandable intervertebral implant. More particularly, a preferred embodiment of the present invention relates to an intervertebral implant that is laterally and vertically expandable in situ from a collapsed, non-expanded or first insertion configuration to a second expanded configuration. The expandable intervertebral implant preferably includes superior and inferior bone contacting members connected together via one or more expandable components such as, for example, a wire netting so that the implant is vertically expandable in the cranio/caudal direction. The superior and inferior bone contacting members preferably are formed by two or more bone contacting components connected together via one or more expandable components such as, for example, a wire netting so that the implant is laterally expandable in the lateral direction if implanted via an anterior approach or laterally expandable in the anterior-posterior direction if implanted via a lateral approach.

The present invention also relates to an associated method of inserting and sequentially expanding the intervertebral implant and an associated method of manufacturing the intervertebral implant such that the intervertebral implant can be manufactured as an integral component.

BRIEF DESCRIPTION OF THE DRAWINGS

The foregoing summary, as well as the following detailed description of the preferred embodiments of the application, will be better understood when read in conjunction with the appended drawings. For the purposes of illustrating the expandable intervertebral implant, surgical method for implanting the intervertebral implant and manufacturing method for forming the intervertebral implant of the present application, there are shown in the drawings preferred embodiments. It should be understood, however, that the application is not limited to the precise arrangements and instrumentalities shown. In the drawings:

FIG. 6A illustrates a top perspective view of a first preferred embodiment of a link member that may be used to form wire netting that may be used in conjunction with the intervertebral implant shown in FIG. 1;

FIG. 6B illustrates a top plan view of the wire netting shown in FIG. 6A, the wire netting illustrated in an at least partially collapsed, non-expanded or first insertion configuration;

FIG. 6C illustrates a top plan view of the wire netting shown in FIG. 6A, the wire netting illustrated in the second expanded configuration;

FIG. 7 illustrates a top perspective view of a second preferred embodiment of a link member that may be used to form wire netting that may be used in conjunction with the intervertebral implant shown in FIG. 1;

FIG. 8 illustrates a top perspective view of a third preferred embodiment of a link member that may be used to form wire netting that may be used in conjunction with the intervertebral implant shown in FIG. 1;

FIG. 9 illustrates a top perspective view of a fourth preferred embodiment of a link member that may be used to form wire netting that may be used in conjunction with the intervertebral implant shown in FIG. 1;

FIGS. 11A-11E illustrate various perspective views of steps of an exemplary surgical method for laterally inserting the expandable intervertebral implant of FIG. 1 in accordance with one aspect of the preferred invention.

DETAILED DESCRIPTION OF ILLUSTRATIVE EMBODIMENTS

Figure 1:
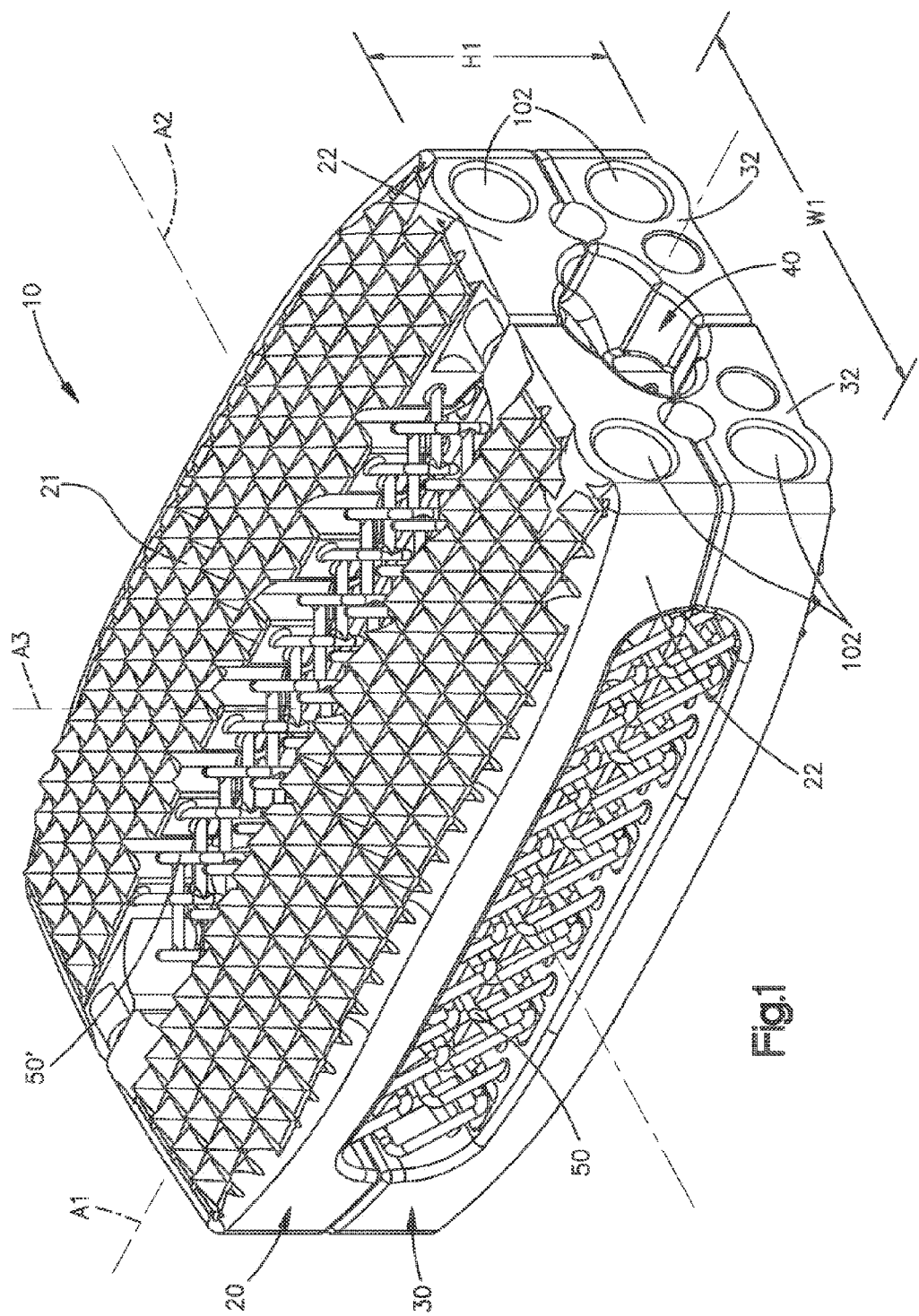
FIG. 1 illustrates a top perspective view of an exemplary intervertebral implant according to the present invention, the implant illustrated in the collapsed, non-expanded or first insertion configuration
Figure 2:
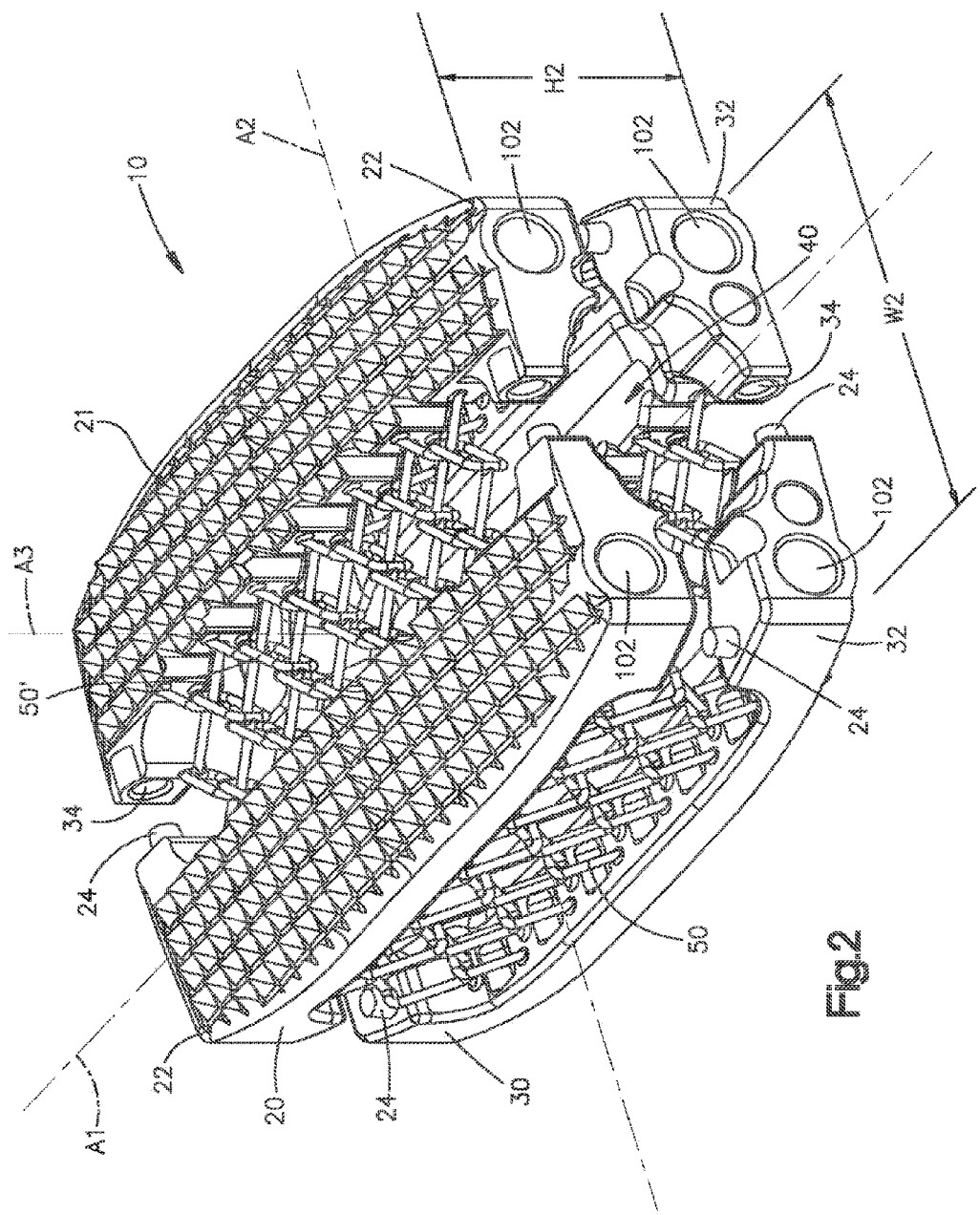
FIG. 2 illustrates a top perspective view of the intervertebral implant shown in FIG. 1, the implant illustrated in a second, expanded configuration.
Figure 3A:
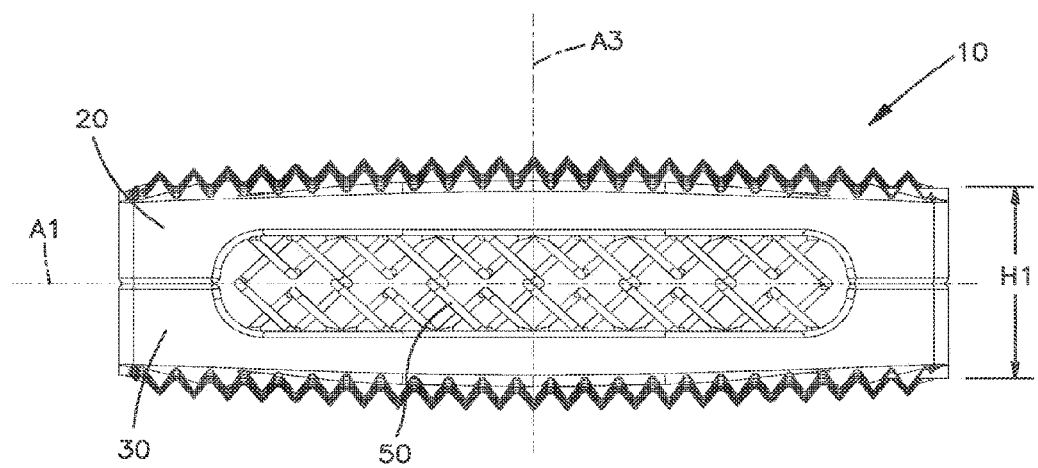
FIG. 3A illustrates a side elevational view of the intervertebral implant shown in FIG. 1, the implant illustrated in the collapsed, non-expanded or first insertion configuration.
Figure 3B:
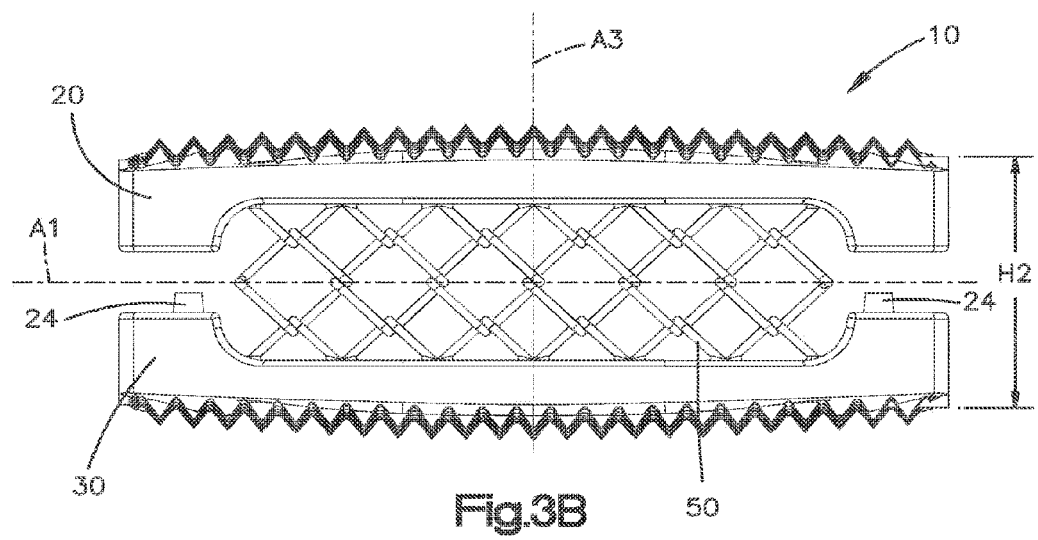
FIG. 3B illustrates a side elevational view of the intervertebral implant shown in FIG. 1, the implant illustrated in the second expanded configuration.
Figure 4A:
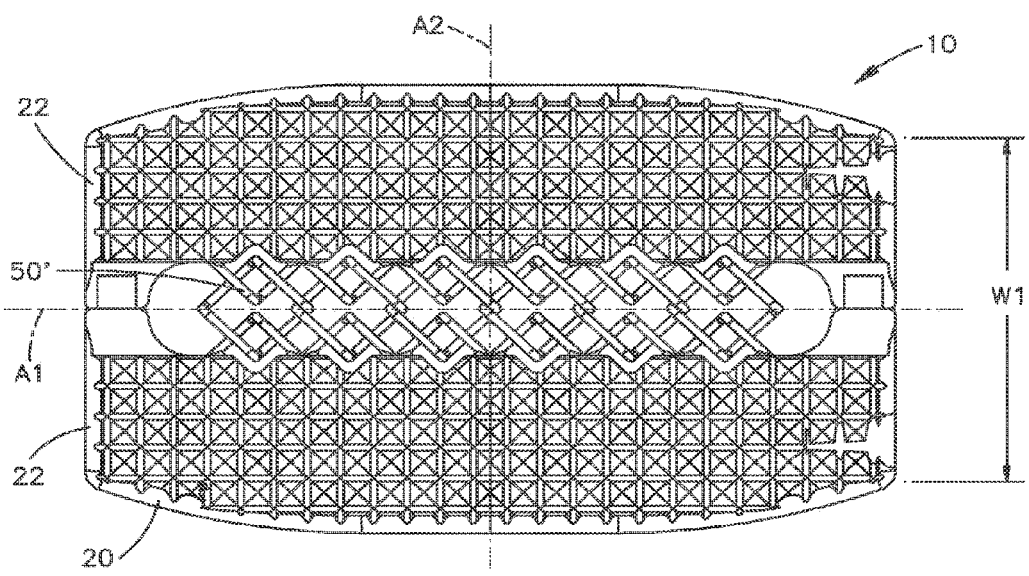
FIG. 4A illustrates a top plan view of the intervertebral implant shown in FIG. 1, the implant illustrated in the collapsed, non-expanded or first insertion configuration.
Figure 4B:
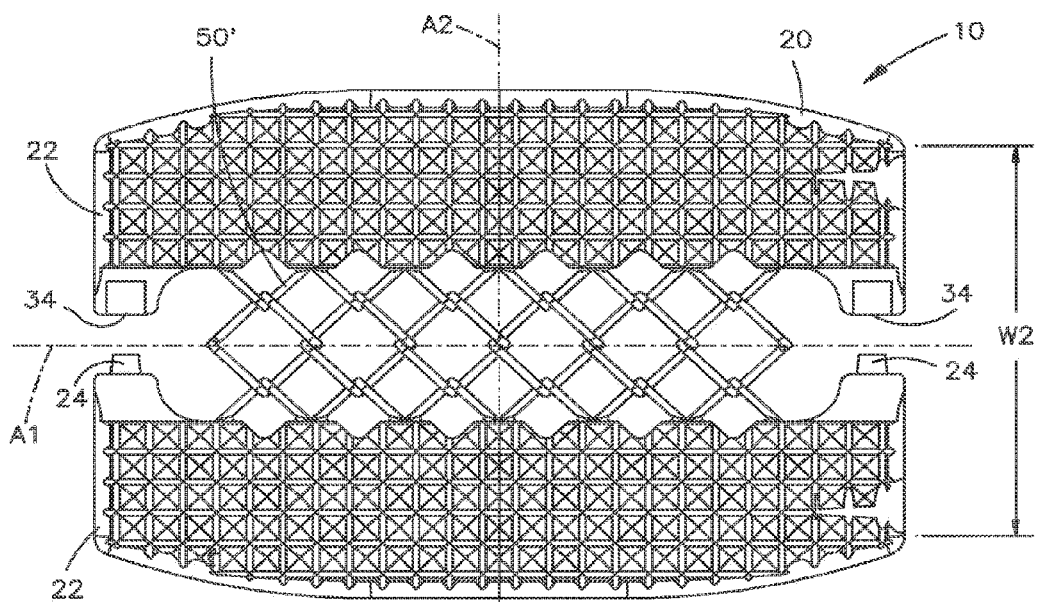
FIG. 4B illustrates a top plan view of the intervertebral implant shown in FIG. 1, the implant illustrated in the second expanded configuration.
Figure 5A:
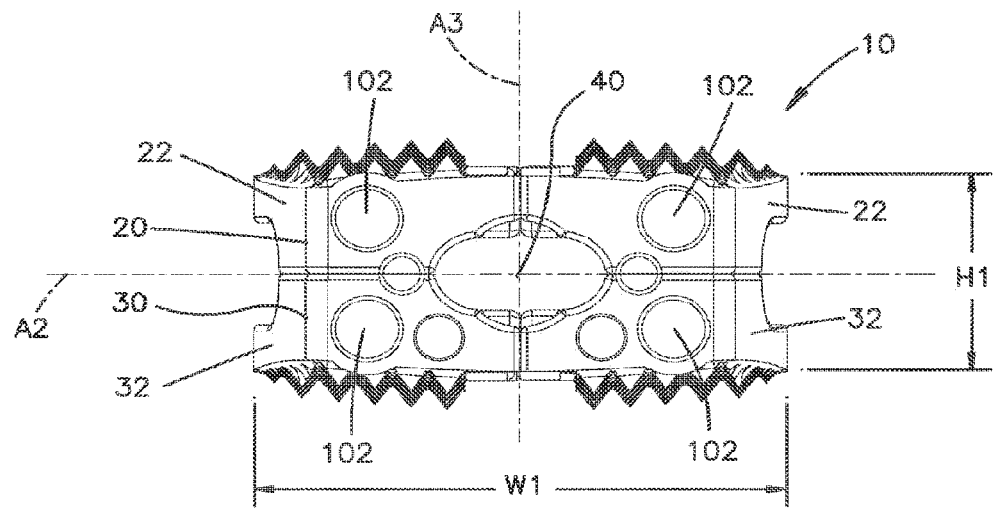
FIG. 5A illustrates a front elevational view of the intervertebral implant shown in FIG. 1, the implant illustrated in the collapsed, non-expanded or first insertion configuration.
Figure 5B:
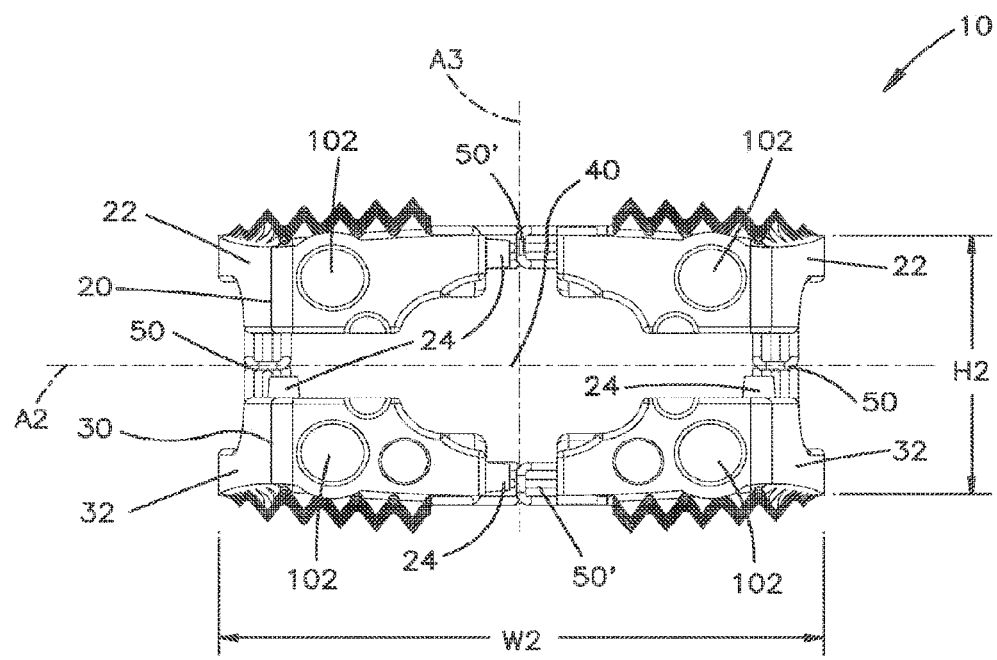
FIG. 5B illustrates a front elevational view of the intervertebral implant shown in FIG. 1, the implant illustrated in the second expanded configuration.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general preferred embodiments of the present invention are directed to (i) an expandable intervertebral implant 10 for implantation between or to replace damaged portions of adjacent vertebral bodies V in a patient's spine (for example, in the lumbar, thoracic or cervical regions), (ii) an exemplary surgical method for implanting the intervertebral implant 10 between adjacent vertebral bodies V in the patient's spine and (iii) an exemplary method of manufacturing the intervertebral implant 10. More specifically, the present invention is preferably directed to an expandable intervertebral implant 10 for total or partial disc or vertebral body V replacement or for nucleus replacement of an intervertebral disc space S. It should be appreciated that while the expandable intervertebral implant 10 of the present application will be described in connection with spinal disc replacement, one of ordinary skill in the art will understand that the implant 10 as well as the components thereof may be used for replacement of tissue in other parts of the body including, for example, knee, hip, shoulder, finger or other joint replacement or for bone augmentation.

Referring to FIGS. 1-5B, as will be described in greater detail below, the expandable intervertebral implant 10 is preferably used for intervertebral support of the spine for patients that require interbody fusion at one or more levels of the spine. The expandable intervertebral implant 10 is preferably implanted by a surgeon into the patient's body in a collapsed, non-expanded or first insertion configuration (as best shown in FIGS. 1, 3A, 4A and 5A), thereby allowing a smaller incision than is typically necessary for implantation of a non-expandable intervertebral implant (not shown). Implantation of the preferred expandable intervertebral implant 10 in the first insertion configuration may also make it easier to insert the implant 10 past structures that may inhibit a surgeon's access to the spine. The expandable intervertebral implant 10 allows surgeons to implant a larger intervertebral implant in the disc space S, generally without having to do an excessive amount of boney resection and soft tissue retraction. Once the implant 10 is inserted into the disc space S, the implant 10 may be expanded to a second expanded configuration (as best shown in FIGS. 2, 3B, 4B and 5B). More preferably, the implant 10 is expandable in the cranio/caudal direction to provide parallel and/or lordotic intervertebral distraction and in the lateral direction. That is, the expandable intervertebral implant 10 is preferably implanted by a surgeon into the patient's body in a collapsed, non-expanded or first insertion configuration wherein the implant has a first height $H_1$ and a first width $W_1$. Thereafter, once inserted into the disc space S, the implant 10 may be expanded to a second expanded configuration wherein the implant 10 has a second height $H_2$ and a second width $W_2$, wherein the second height $H_2$ and the second width $W_2$ are larger than the first height $H_1$ and the first width $W_1$, respectively.

The preferred expandable intervertebral implant 10 may, for example, fill the entire intervertebral disc space S to replace the entire intervertebral disc. Alternatively, a plurality of expandable intervertebral implants 10 may be used to fill the intervertebral disc space S. For example, two or more smaller expandable intervertebral implants 10 may be used to fill the intervertebral disc space S. Alternatively, the expandable intervertebral implant 10 may be sized and configured to only partially replace an intervertebral disc space S, such as for example, to replace a nucleus. In addition, the preferred intervertebral implant 10 may be configured to replace a disc and a portion of a damages vertebra V.

The expandable intervertebral implant 10 preferably includes a superior bone contacting member 20 for contacting a first, superior vertebra V, an inferior bone contacting member 30 for contacting a second, inferior vertebra V and a vertical wire netting or mesh 50 for interconnecting the superior and inferior bone contacting members 20, 30 with respect to one another. The vertical wire netting 50 preferably enables the superior and inferior bone contacting members 20, 30 to move (e.g., expand) in the cranial/caudal direction or generally away from each other during movement from the collapsed, non-expanded or first insertion configuration to the second expanded configuration when the implant 10 is inserted into the disc space S. The superior and inferior bone contacting members 20, 30 are sized and configured to contact at least a portion of the endplates of the superior and inferior vertebral bodies V, respectively, or to engage a surface of the superior and/or inferior vertebral bodies V remaining after damaged portions of the superior and/or inferior vertebrae V are removed from the spine. The superior and inferior bone contacting members 20, 30 preferably define a cavity 40 therebetween.

The superior bone contacting member 20 of the exemplary preferred embodiment is formed by two or more bone contacting components 22 interconnected by a lateral wire netting or mesh 50'. Similarly, the inferior bone contacting member 30 of the exemplary preferred embodiment is formed by two or more bone contacting components 32 interconnected by the lateral wire netting 50'. That is, the superior and inferior bone contacting members 20, 30 are each preferably constructed by a plurality of generally rigid bone contacting components 22, 32 separated by or interconnected by the lateral expandable wire netting 50' so that the bone contacting components 22, 32, which form the bone contacting members 20, 30, are moveable (e.g., expandable) with respect to one another. As shown, the bone contacting components 22, 32 preferably are in the form of one or more plates, more preferably an L-shaped plate, although other shapes are contemplated. However, the bone contacting members 20, 30 may be constructed as a single integral component, for example, if the implant 10 is constructed to expand only in the cranial/caudal direction. In addition, the superior and inferior bone contacting members 20, 30 may have convex-shaped surfaces wherein they contact the endplates of the vertebra V to conform to the shape of the endplates.

In this manner, by incorporating the vertical wire netting 50 between the superior and inferior bone contacting members 20, 30, the implant 10 is expandable from the collapsed, non-expanded or first insertion configuration wherein the implant 10 has a first height $H_1$ to the second expanded configuration wherein the implant 10 has a second height $H_2$, wherein the second height $H_2$ is larger than the first height $H_1$. Similarly, by incorporating the lateral wire netting 50' between the adjacent bone contacting components 22, 32, which form the superior and inferior bone contacting members 20, 30, respectively, the implant 10 is expandable from the collapsed, non-expanded or first insertion configuration wherein the implant 10 has a first width $W_1$ to a second expanded configuration wherein the implant 10 has a second width $W_2$, wherein the second width $W_2$ is larger than the first width $W_1$. That is, the lateral wire netting 50' preferably enables the bone contacting components 22, 32 to be laterally moveable (e.g., in the anterior-posterior or lateral direction depending on insertion procedure) with respect to one another along a lateral axis A2 while the vertical wire netting 50 enables the superior and inferior bone contacting members 20, 30 to be vertically moveable with respect to one another along a vertical axis A3. In addition, the vertical and lateral wire netting 50, 50' enables the superior bone contacting member 20 to move with respect to the inferior bone contacting member 30 along a longitudinal axis A1. Thus, the vertical and lateral wire netting 50, 50' enables the implant 10 to conform its final shape in the second or expanded configuration to mate to the typically uneven surfaces of the endplates of the vertebral bodies V. In addition, the vertical and lateral wire netting 50, 50' enables the implant 10 to limit stress risers at contact points between the implant 10 and the vertebral bodies V thus making the preferred implant 10 applicable for insertion between osteoporotic bone.

That is, in the preferred embodiment, by forming the preferred implant 10 from four bone contacting components 22, 32 interconnected by vertical and lateral wire netting 50, 50', the superior and inferior bone contacting members 20, 30 of the implant 10 are preferably able to move in six degrees of freedom with respect to each other. Specifically, the superior and inferior bone contacting members 20, 30 are able to move longitudinally relative to each other along the longitudinal axis A1, laterally relative to each other along the lateral axis A2, vertically relative to each other along the vertical axis A3, pivot or roll relative to each other about the longitudinal axis A1, pivot or pitch relative to each other about the lateral axis A2 and pivot or yaw relative to each other about the vertical axis A3. Accordingly, the preferred implant 10 is able to conform its final shape in the second or expanded configuration to mate to the typically uneven surfaces of the endplates of the vertebral bodies V and limit stress risers at contact points between the implant 10 and the vertebral bodies V.

It should be noted that it is also envisioned that the superior and inferior bone contacting members 20, 30 may be formed of four or more bone contacting components 22, 32 interconnected by lateral wire netting 50' and longitudinal wire netting (not shown) so that the implant 10 is longitudinally moveable from a first length to a second length (not shown). Alternatively, the superior and inferior bone contacting members 20, may be formed of two bone contacting components 22, 32 interconnected by longitudinal wire netting (not shown) but not lateral wire netting 50' so that the implant 10 is longitudinally moveable from a first length to a second length (not shown) but not laterally moveable from the first width $W_1$ to the second width $W_2$.

The vertical wire netting 50 and the lateral wire netting 50', preferably enable approximately three tenths of a millimeter (0.3 mm) to approximately twelve millimeters (12 mm) of movement, although other amounts of movement are permissible as would be apparent to one having ordinary skill in the art. Further, the implant is not limited to having the generally rectangular or box-shaped configuration shown in FIGS. 1-12L, for example, the implant 10 may have a generally circular or cylindrical-shaped series of rings that form the superior and inferior bone contacting members 20, 30 separated by wire netting such that an inner ring may expand along the vertical axis A3 further than an outer ring to conform to a concave-shaped endplate.

Referring to FIGS. 6A-6C, a first preferred, exemplary embodiment of the vertical and/or lateral wire netting 50, 50' is formed by interconnecting a plurality of individual first link members 52. As shown, the plurality of individual first link members 52 may have a generally rectangular shape when at least partially expanded but are not so limited.

Referring to FIG. 7, a second preferred exemplary embodiment of the lateral and/or vertical wire netting 50, 50' may be formed by interconnecting a plurality of individual second link members 52' wherein the plurality of individual second link members 52' have a generally trapezoidal shape when at least partially expanded but are not so limited. Referring to FIG. 8, a third preferred, exemplary embodiment of the vertical and/or lateral wire netting 50, 50' may be formed by interconnecting a plurality of individual third link members 52" wherein the plurality of individual think link members 52" have an alternate, second rectangular shape when at least partially expanded but are not so limited. Referring to FIG. 9, a fourth preferred, exemplary embodiment of the vertical and/or lateral wire netting 50, 50' may be formed by interconnecting a plurality of individual fourth link members 52' wherein the plurality of individual fourth link members 52''' have an alternate, third rectangular shape when at least partially expanded but are not so limited. Alternatively, the vertical and/or lateral wire netting 50, 50' may have any other form or shape such as, for example, a plastically deformable material, mesh, stent, etc. so long as the vertical and/or lateral wire netting 50, 50' interconnects and enables the superior and inferior bone contacting members 20, and/or the superior and inferior bone contacting components 22, 32 to move with respect to one another. The preferred individual link members 52, 52', 52", 52''' are not limited to the generally rectangular or trapezoidal shapes and may take nearly any shape such as, for example, oval, circular, triangular, hexagonal, etc.

Figure 10A:
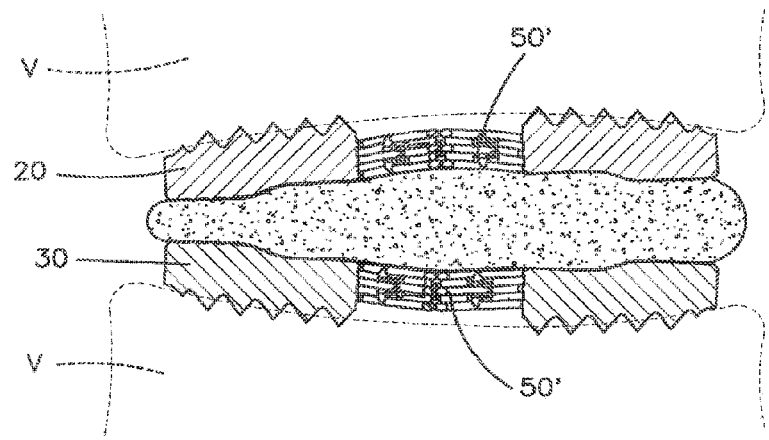
FIGS. 10A-10C illustrate various cross-sectional views of the intervertebral implant shown in FIG. 1, the superior and inferior bone contacting members incorporating wire netting so that the superior and inferior bone contacting members are able to adapt and/or conform to the endplates of the superior and inferior vertebral bodies V, respectively.
Figure 10B:
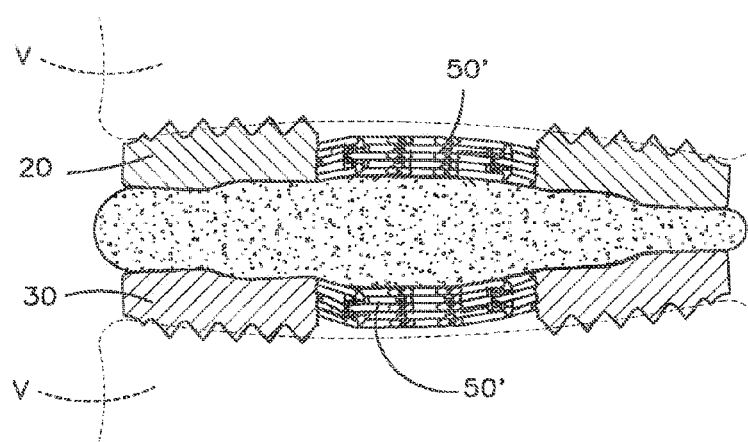
Figure 10C:
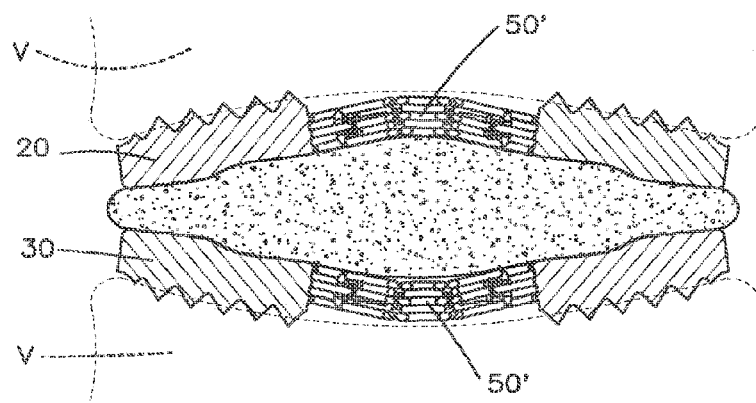

In addition, by forming or constructing the vertical and/or lateral wire-netting 50, 50' from a plurality of preferred individual first, second, third and/or fourth link members 52, 52', 52", 52''' the superior and/or inferior bone contacting components 22, 32 are able to tilt or generally move with respect to one another so that the superior and inferior bone contacting members 20, 30 are better able to conform to the configuration of the endplates of the adjacent vertebral bodies V. That is, as previously described above, by forming the preferred implant 10 from four bone contacting components 22, 32 interconnected by vertical and lateral wire netting 50, 50', the flexible of the vertical and/or lateral wire netting 50, 50' enables the superior and inferior bone contacting members 20, 30 of the implant 10 to move in six degrees of freedom with respect to each other so that the implant 10 and more particularly the superior and inferior bone contacting members 20, 30 are better able to adapt and/or conform to the anatomical shape of the endplates of the superior and inferior vertebral bodies V, respectively. As illustrated in FIGS. 10A-10C, the superior and inferior bone contacting components 22, 32 are better able to adapt and/or conform to the endplates of the superior and inferior vertebral bodies V, respectively, due to the inherent flexibility or adaptability of forming the superior and inferior bone contacting members 20, 30 from multiple components 22, 32 interconnected by a flexible wire netting 50, 50'. Thus, in use, the lateral wire netting 50' enables the superior bone contacting components 22 to move with respect to one another and enables the inferior bone contacting components 32 to move with respect to one another such that the lateral wire netting 50' enables the superior and inferior bone contacting members 20, 30 to adapt and/or conform to the endplates of the superior and inferior vertebral bodies V, respectively.

The preferred implant 10 also includes a cavity 40 located between the superior and inferior bone contacting members 20, 30. The cavity 40 is preferably sized and configured to receive a filling material (not shown) and/or a balloon 75, an expansion sack, an expansion bag, etc. (collectively referred to herein as an "expansion member"). The expansion member 75 is preferably sized and configured to be received within the cavity 40 in order to limit any filling material from overflowing and escaping from the cavity 40. More preferably, as will be described in greater detail below, once the implant 10 has been implanted and positioned, the expansion member 75 is preferably inserted into the cavity 40. Thereafter, the filling material may be inserted into the expansion member 75, expanding the expansion member 75 so that the implant 10 is expanded from the collapsed, non-expanded or first insertion configuration to the second expanded configuration. Once inserted, the filling material preferably hardens or is cross-linked in order to support the implant 10 in the second expanded configuration. Alternatively, the filling material may not harden and may partially harden into a gel-like material or may retain a flowable or liquid state and become sealed in the expansion member 75.

It should be noted that expanding of the expansion member 75 may or may not cause distraction of the adjacent vertebral bodies V. However, the flexibility of the expansion member 75 and the sequential hardening of the filling material preferably provide a geometrically adapted restoration of the intervertebral disc space S. Alternatively, the filling material may remain in a gel and/or liquid state and may be sealed in the expansion member 75. In addition, as will be generally appreciated by one of ordinary skill in the art, the expansion member 75 may be inserted into the cavity 40 prior to implantation of the implant 10, the filling material may be injected into the expansion member 75 prior to implantation of the implant 10, the expansion member 75 may be integrated with or coupled to the implant 10, and/or the expansion member 75 may be omitted entirely.

Moreover, it should be understood that the superior and inferior bone contacting members 20, 30 may include any number of bone contacting components 22, 32 and interconnecting lateral wire netting 50' such as, for example, three bone contacting components 22, 32 interconnected by two lateral wire nettings 50'. It is also envisioned that the implant 10 may include one or more intermediate components (not shown) between the superior and inferior bone contacting members 20, 30. The intermediate components may be coupled to the superior and inferior bone contacting members 20, 30 via the vertical wire netting 50. Moreover, it is also envisioned that the implant 10 may include the vertical wire netting 50 to enable cranio/caudal expansion without incorporating the lateral wire netting 50'. Alternatively, the implant 10 may include the lateral wire netting 50' to enable lateral expansion without incorporating the vertical wire netting 50.

The superior and inferior bone contacting members 20, 30 may include means for increasing the stability of the implant 10, such as, for example, one or more projections, one or more roughened surfaces, one or more undulating structures, one or more ridges, one or more keels, etc. Preferably, the superior and inferior bone contacting members 20, 30 include a plurality of teeth 21 for increasing the stability of the implant 10.

The implant 10 may also include a mechanism or feature for engaging an implant insertion instrument (not shown). The mechanism or feature for engaging the insertion instrument may take on any form now or hereafter known including, for example, one or more bores 102 for receiving one or more projections (not shown) formed on the implant insertion instrument, one or more projections (not shown) for engaging one or more bores (not shown) formed on the implant insertion instrument, one or more channels (not shown) for receiving one or more tips formed on the implant insertion instrument, one or more threaded bores (not shown) for receiving one or more threaded shafts or screws, etc.

The implant 10 may also include a mechanism or features for reducing and/or preventing shearing or dismantling of the implant 10 during insertion such as, for example, the superior and inferior bone contacting members 20, 30 may include interconnecting projections 24 and bores 34 for temporarily securing the implant 10 in its collapsed or insertion configuration.

The superior and inferior bone contacting members 20, 30 may be formed from any biocompatible material including, but not limited to, a metal, such as, for example, cobalt-chromium-molybdenum (CCM) alloys, titanium, titanium alloys, stainless steel, aluminum, etc., a ceramic such as, for example, zirconium oxide, silicone nitride, etc., an allograft, an autograft, a metal-allograft composite, a polymer such as, for example, polyaryl ether ketone (PAEK), polyether ether ketone (PEEK), polyether ketone ketone (PEKK), polyetherketone (PEK), polyetherketone ether-ketone-ketone (PEKEKK), etc. The polymers may be reinforced with a fiber such as, for example, a carbon fiber or other thin, stiff fiber.

The superior and inferior bone contacting members 20, 30 may also be coated in order to enhance their osteo-conductive properties. For example, the bone contacting members 20, 30 may be coated with an etching, anodization, an anodic plasma chemical process, electrolytic deposition, plasma spraying, a thin layer of titanium (Ti) via a physical or chemical vapor deposition process, an anodic plasma chemical surface treatment incorporating, for example, Ca and/or P in the Ti-Oxide surface layer or via a Ti or HA plasma spray, etc.

The expansion member 75 may be manufactured from any biocompatible material including, but not limited to, a polyurethane, a polycarbonate urethane, a poly carbonate-silicone urethane copolymer, polyamine, polyethylene terephthalate (PET), polycaprolactone, etc.

The filling material may be any biocompatible material known in the art and may be a rigid or elastic material. The filling material may be comprised of, for example, a bone cement, a hydrogel, a polyvinyl alcohol, a sodium polyacrylate, an acrylate polymer, a methyl-methacrylate, a co-polymer with an abundance of hydrophilic groups, p-vinyl pyrollidone, polyethyleneimine, etc., a setting or curing hydrogel based co-polymer such as, for example, polyethyleneimine, poly(diethylaminoethyl methacrylate), poly (ethylaminoethyl methacrylate), etc., a thermally setting hydrogel based co-polymers, such as, for example, poly-N-isopropylacrylamide with polyethylene glycol, copolymers of polyethylene oxide and polyphenelylene oxide, copolymers of polyethylene glycol and polyactides, etc., an ionic setting hydrogel such as, for example, ethylacrylate, methacrylic acid, 1,4-butanediacrylate, etc., or a PCU, PCU-silicone co-polymer, silicone or other non-resorbable pure or elastic co-polymer (e.g., PCU's silicone end group modified PU's, RTV curing siloxane based elastomers, etc.).

Exemplary Method of Inserting the Intervertebral Implant.

The expandable intervertebral implant 10 may be inserted within the targeted intervertebral disc space S by any means, method, or approach now or hereafter known in the art including, but not limited to, via anterior, lateral, posterior, anterior-lateral, or posterior-lateral approaches, etc. Preferably, the implant 10 is implanted using a minimally invasive technique. Alternatively, the implant 10 may be implanted via an open incision, as would be appreciated by one having ordinary skill in the art.

Figure 11A:
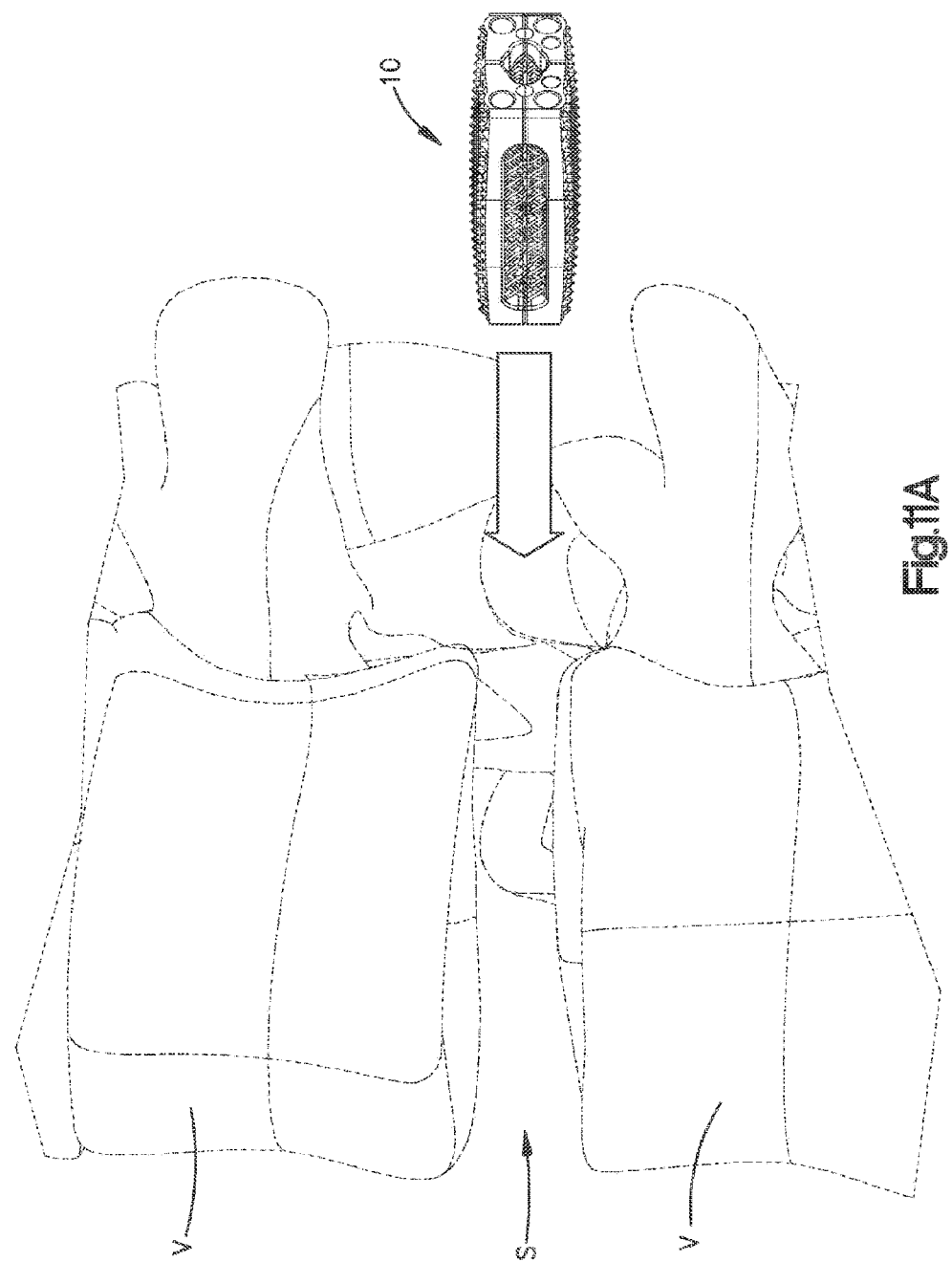
Figure 11D:
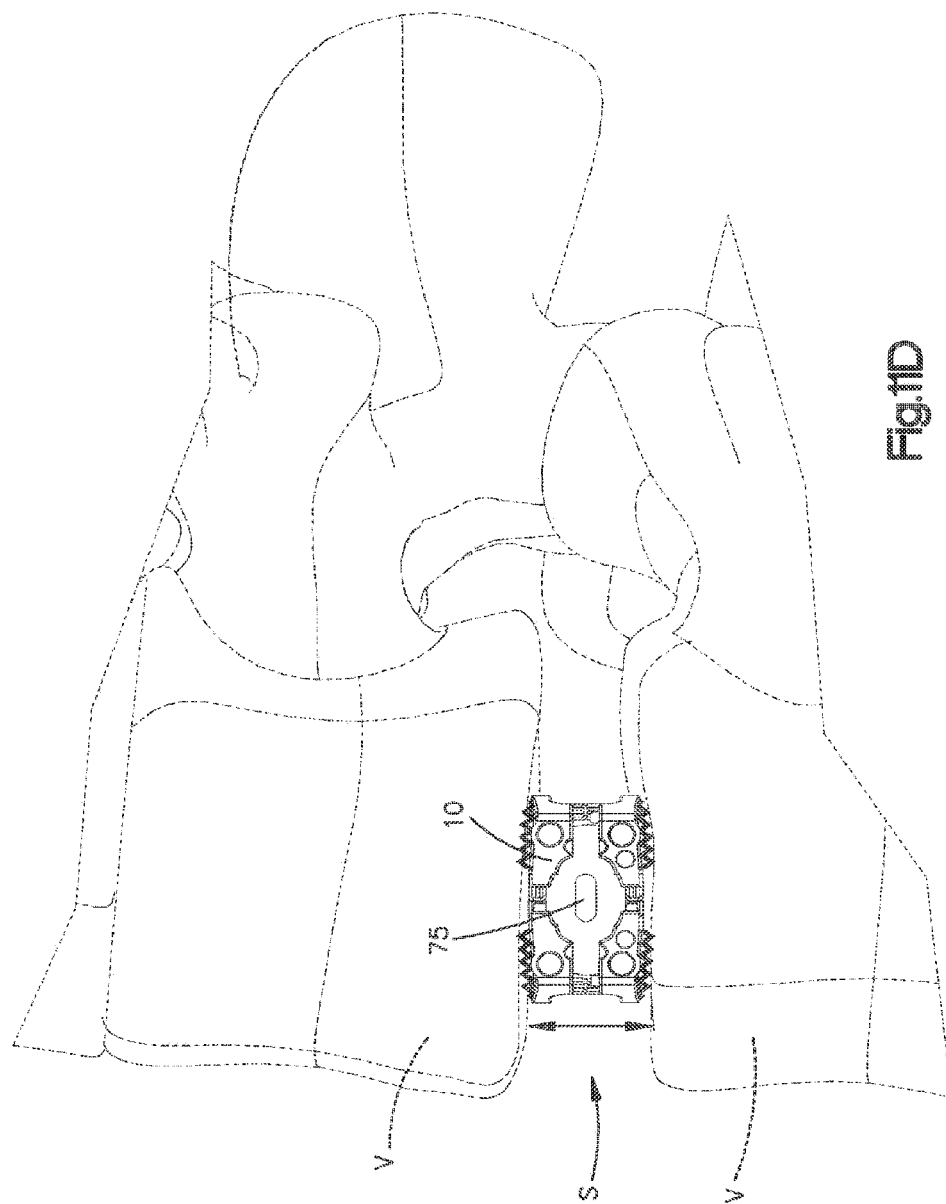
Figure 12A:
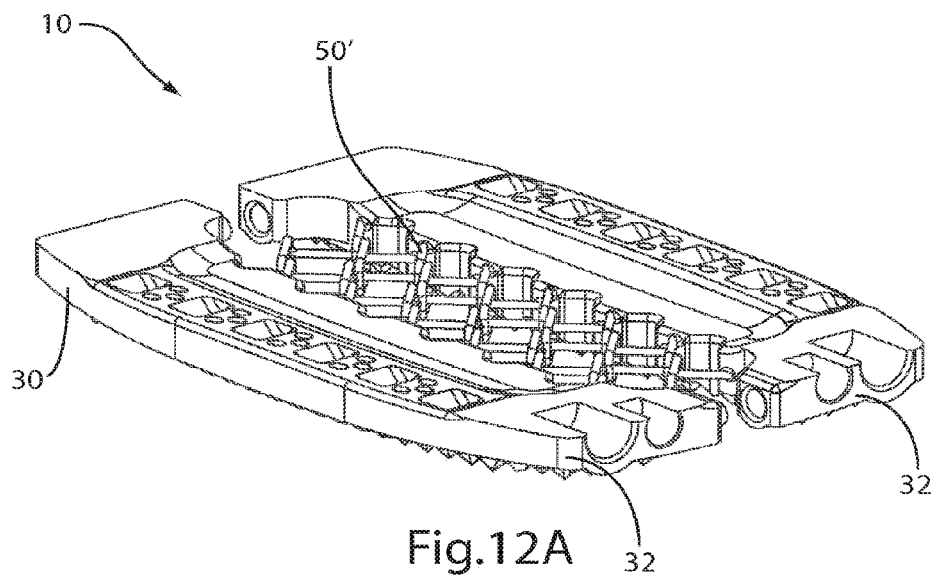
FIGS. 12A-12L illustrate various top, perspective views of steps of an exemplary method for manufacturing the expandable intervertebral implant of FIG. 1 in accordance with one aspect of the preferred invention.
Figure 12B:
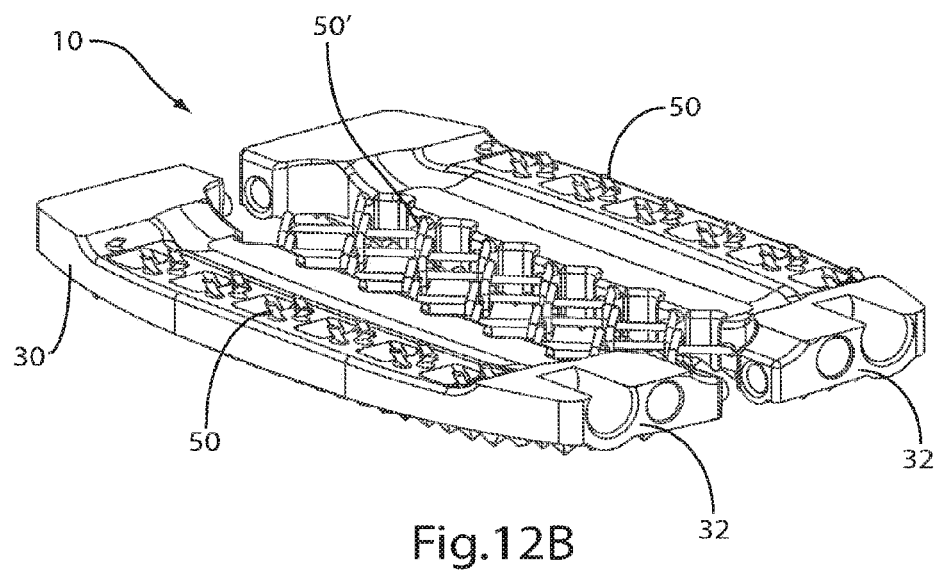
Figure 12C:
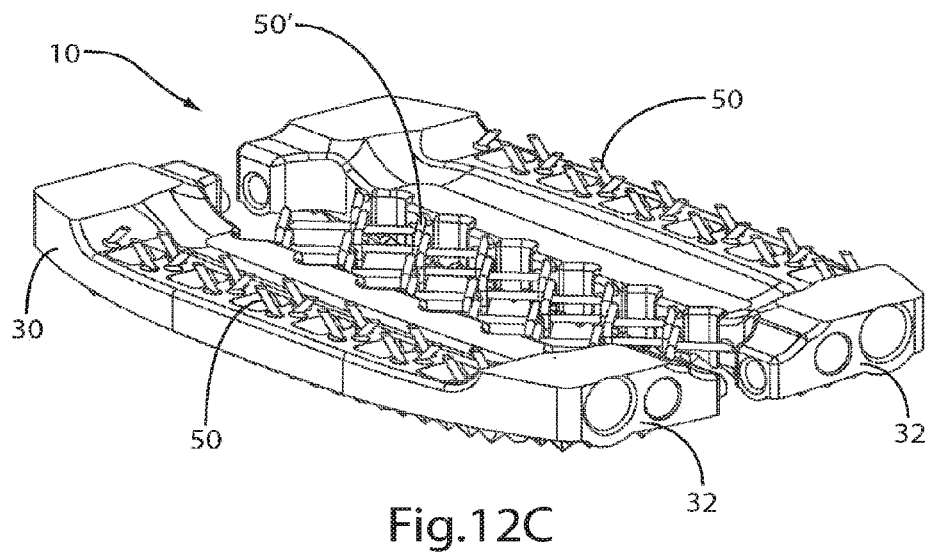
Figure 12D:
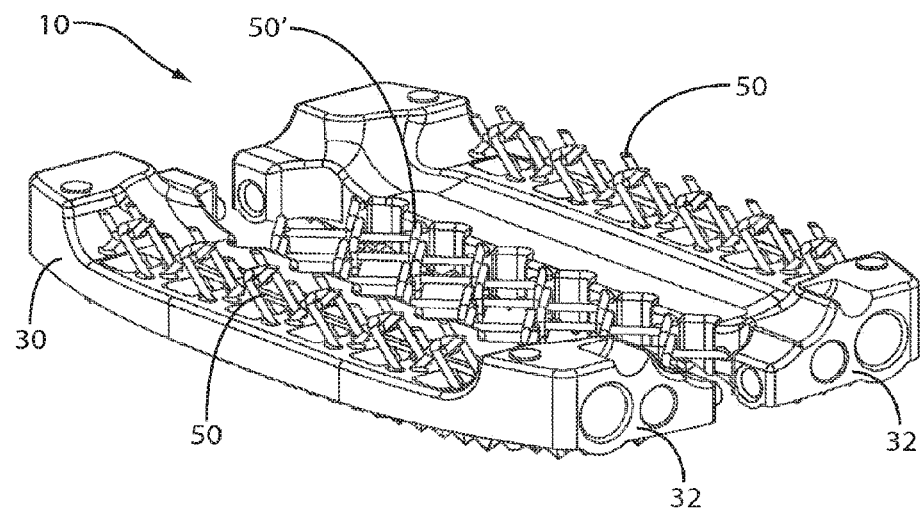
Figure 12E:
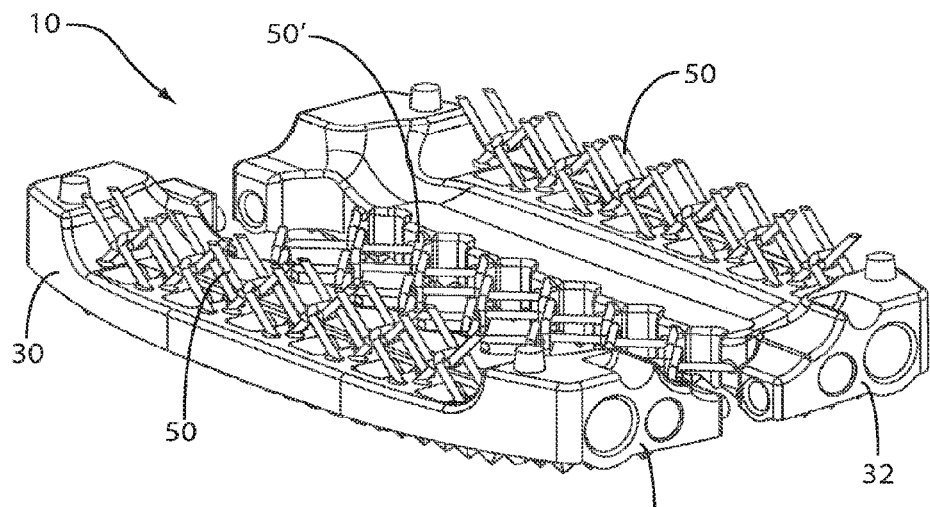
Figure 12F:
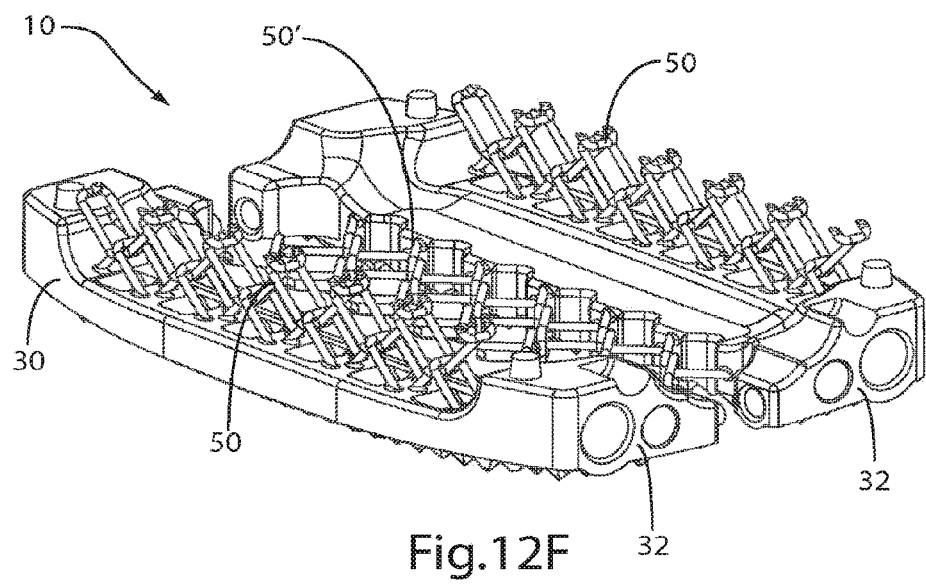
Figure 12G:
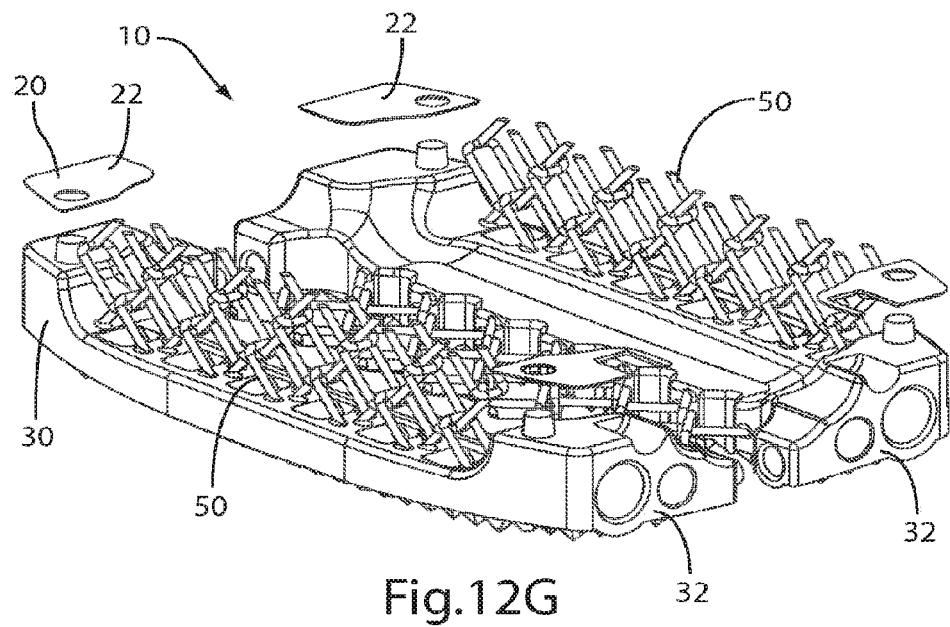
Figure 12H:
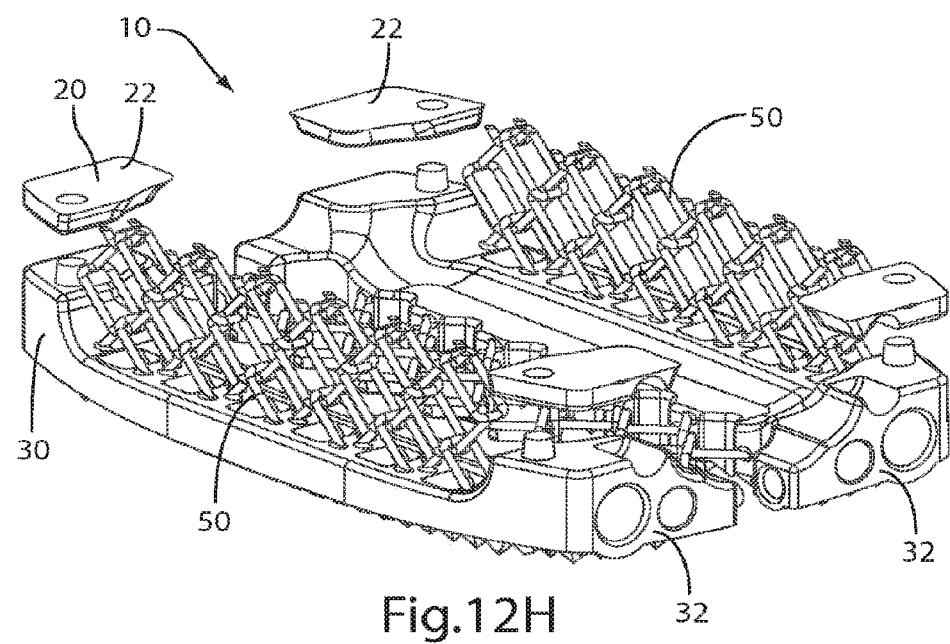
Figure 12I:
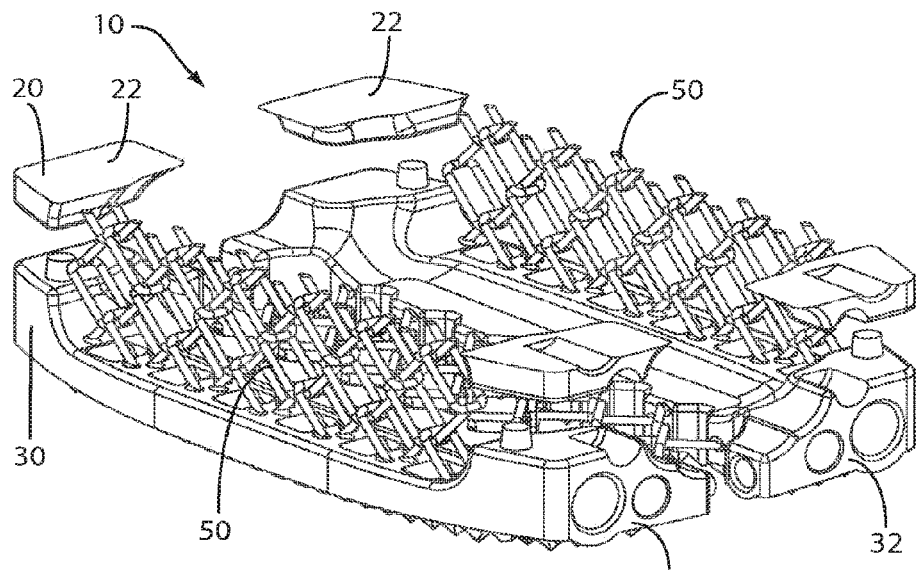
Figure 12J:
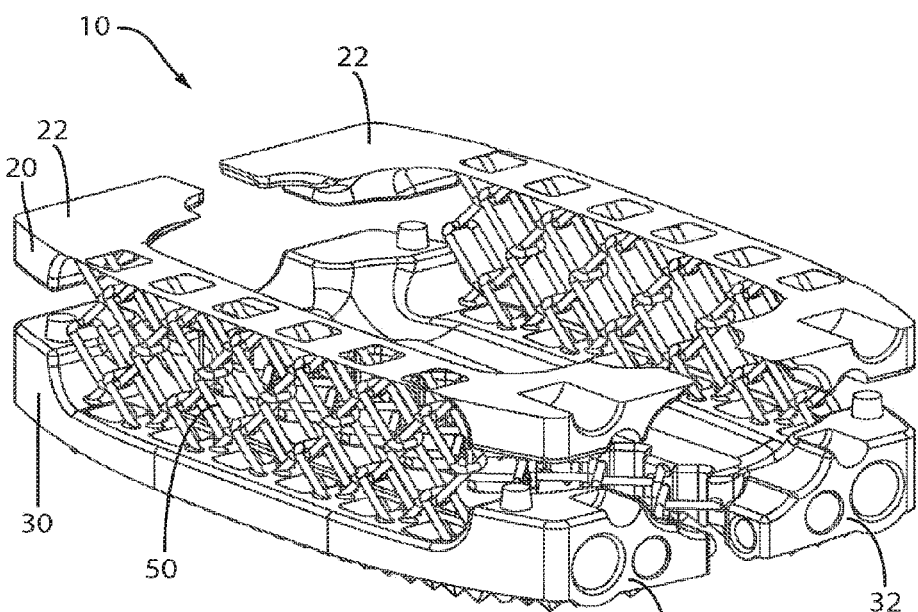
Figure 12K:
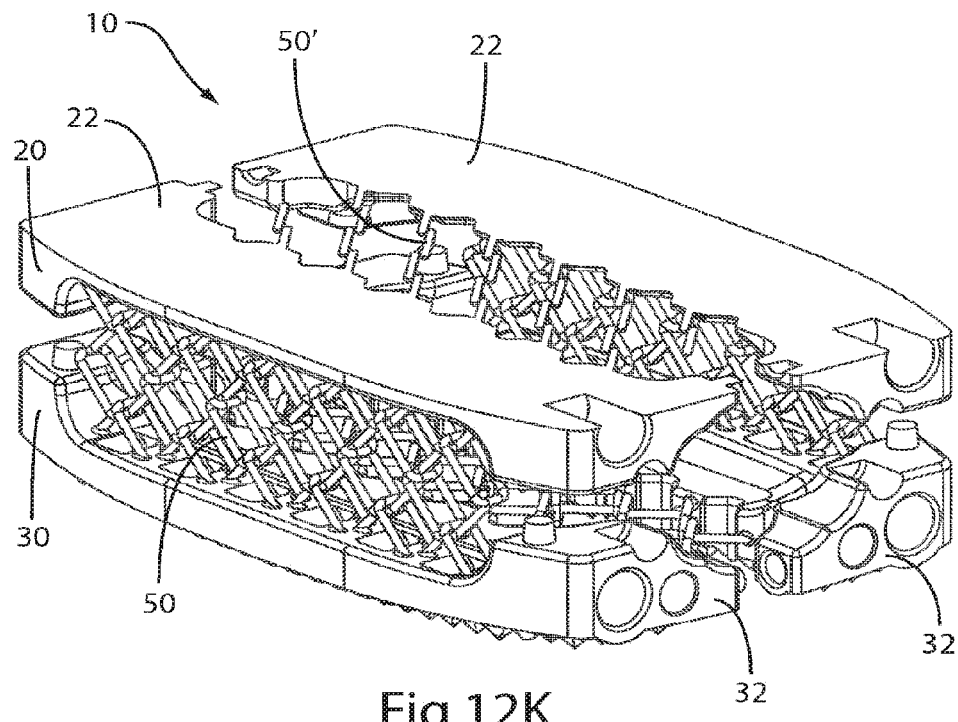
Figure 12L:
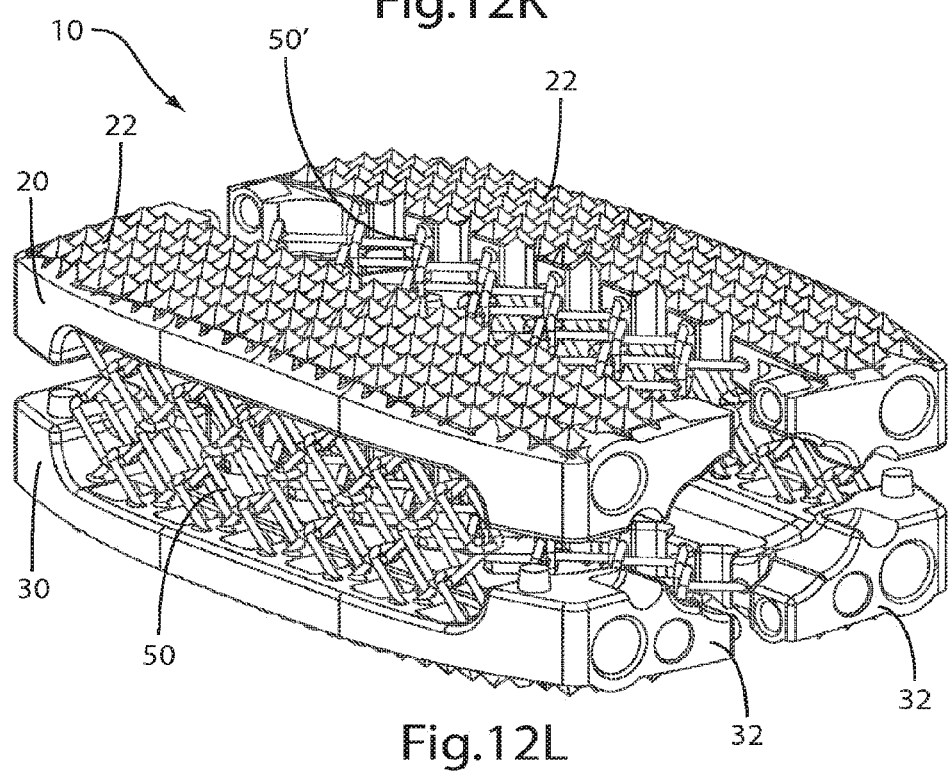

Referring to FIGS. 11A-11E, in one exemplary method of inserting the implant 10 via a lateral approach, the implant 10 is inserted into the intervertebral disc space S between adjacent superior and inferior vertebral bodies V via an insertion instrument (not shown). As illustrated in FIG. 11A, the implant 10 is preferably inserted into the intervertebral disc space S in the collapsed, non-expanded or first insertion configuration following a preferably minimal incision through the skin to the disc space S. As illustrated in FIG. 11B, the implant 10 is preferably positioned within the intervertebral disc space S at least partially in a posterior direction in order to generally keep the motion segment in balance. More preferably, the implant 10 should be positioned so that the implant 10 engages the stronger peripheral aspects of the adjacent vertebral bodies V. Once the implant 10 has been properly positioned in its desired location, as illustrated in FIG. 11C, the implant 10 is preferably laterally expanded in the anterior-posterior direction (in the lateral direction if the implant 10 was inserted via an anterior or posterior approach) via a surgical instrument (not shown). Alternatively, the implant 10 may be inserted with the expansion member or balloon 75 therein and laterally expanded via the expansion member 75. Preferably, the implant's position should be checked at this point to ensure preferred positioning. Once the position of the implant 10 is verified based generally on surgeon preference and/or physiology, as illustrated in FIG. 11D, the expansion member 75 is inserted and positioned within the cavity 40 formed in the implant 10 via an insertion instrument (not shown). The implant 10 may be slightly expanded via the implant insertion instrument in order to ease insertion of the expansion member 75 within the cavity 40, if necessary. Next the expansion member 75 is filled with a filling material, which causes the implant 10 to expand in the cranio/caudal direction, preferably resulting in the implant 10 firmly penetrating into the endplates of the adjacent superior and inferior vertebral bodies V. Due to the adaptability of the vertical and/or lateral wire netting 50, 50', the superior and inferior bone contacting members 20, 30 of the implant 10 may substantially mate to the typically uneven surfaces of the endplates of the superior and inferior vertebral bodies V, respectively. For example, the individual bone contacting members 22, 32 may move linearly relative to each other along the longitudinal, lateral and/or vertical axes A1, A2, A3 and may pivot relative to each other about the longitudinal, lateral and/or vertical axes A1, A2, A3 such that the shape of the implant 10 in the expanded configuration conforms to the anatomical shape of the pre-existing endplates of the vertebrae V. Specifically, each of the bone contacting members 22, 32 are movable relative to each other in six degrees of freedom to permit the individual components to adapt their final position to the patient's anatomy, thereby reducing stress risers that may develop when an implant is unable to conform to the shape of the anatomy.

Exemplary Method of Manufacturing the Intervertebral Implant

The preferred expandable intervertebral implant 10 may be manufactured by any means and/or method now or hereafter known in the art including, but not limited to, by manufacturing each of the bone contacting members 20, 30 as separate and distinct components and then coupling each of the components to vertical and lateral wire netting 50, 50', as required.

Preferably, however, the implant 10 is formed as an integral implant manufactured via a layer-wise or layer by layer manufacturing process. For example, referring to FIGS. 12A-12L, the implant 10 preferably is manufactured via a selective laser melting process. The metal components are preferably set up in layers, similar to a stereo-lithograph. In use, a thin layer of metal powder is applied to a platform. The powder is then locally melted by, for example, a laser beam. The platform is then lowered by a defined layer height. Another thin layer of metal powder is then applied. The second layer of powder is then locally melted. This process is repeated until the implant 10 is complete. The ability to manufacture the implant 10 as a single or integral component or part permits the manufacture of continuous loops or solid vertical and lateral wire netting 50, 50' between the bone contacting components 22, 32. In contrast, alternate techniques for constructing the vertical and lateral wire netting 50, 50' may require joining together of ends of the wires to construct the preferred first, second, third and fourth link members 52, 52', 52", 52'".

Alternatively, the implant 10 may be manufactured via a selective laser sintering process. Generally, the laser sintering process follows the same steps as the selective laser melting process described above. However since sintering is performed below the melting point of the substrate material, the laser sintering process allows the original metal powder to be mixed with a binding agent. A steam stripping process may be used after the laser sintering process. Using the laser sintering process, combinations of metals as well as microporous structures can be manufactured. The laser sintering process may also be used in connection with thermoplastic polymers which do not have any specific melting point but rather have a transition zone between a glass transition temperature and a melt mass temperature.

While laser melting and sintering processes have been described, other manufacturing methods are contemplated including, but not limited to, other methods of curing or sintering such as, for example, the use of ultrasonic or ultraviolet rays.

Features described herein may be used singularly or in combination with other features. In addition, features disclosed in connection with one embodiment may be interchangeable with a feature or features disclosed in another embodiment. Therefore the presently disclosed embodiments are to be considered as illustrative and not restrictive, the scope of the invention being indicated by the appended claims, and not limited to the foregoing description.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

What is claimed:

1. An expandable intervertebral implant configured to be implanted into an intervertebral space defined between a superior vertebra and an inferior vertebra, the expandable intervertebral implant comprising:

a superior bone contacting member that defines a superior portion of a proximal terminal end of the implant and a superior portion of a distal terminal end of the implant that is opposite the proximal terminal end of the implant along a longitudinal direction, the superior bone contacting member defining a superior bone facing surface configured to face the superior vertebra when the implant is disposed in the intervertebral space, the superior bone contacting member including a first superior bone contacting component, a second superior bone contacting component spaced from the first superior bone contacting component along a lateral direction that is perpendicular to the longitudinal direction, wherein the superior bone contacting member defines a superior abutment surface;

a first expandable lateral component interconnected between the first and second superior bone contacting components along the lateral direction, wherein the first superior bone contacting component defines a first inner surface and a first outer surface opposite the first inner surface along the lateral direction, the second superior bone contacting component defines a second inner surface and a second outer surface opposite the second inner surface along the lateral direction, the first and second inner surfaces face each other, and the first expandable lateral component extends from the first inner surface to the second inner surface;

an inferior bone contacting member that defines an inferior portion of each of the proximal terminal end and the distal terminal end, the inferior bone contacting member defining an inferior bone facing surface configured to face the inferior vertebra when the implant is disposed in the intervertebral space, the inferior bone contacting member spaced from the superior bone contacting member in a vertical direction that is perpendicular to both the lateral direction and the longitudinal direction, the inferior bone contacting member including a first inferior bone contacting component, a second inferior bone contacting component spaced from the first inferior bone contacting component along the lateral direction, wherein the inferior bone contacting member defines an inferior abutment surface;

a second expandable lateral component interconnected between the first and second inferior bone contacting components along the lateral direction, wherein the first inferior bone contacting component defines a third inner surface and a third outer surface opposite the third inner surface along the lateral direction, the second inferior bone contacting component defines a fourth inner surface and a fourth outer surface opposite the second inner surface along the lateral direction, the third and fourth inner surfaces face each other, and the second expandable lateral component extends from the third inner surface to the fourth inner surface; and at least one expandable vertical component interconnected between the superior and inferior bone contacting members along the vertical direction, wherein the implant is expandable in situ in both the vertical direction and the lateral direction from a first insertion configuration to a second expanded configuration, whereby 1) the first expandable lateral component expands along the lateral direction as respective entireties of the first superior bone contacting component and the second superior bone contacting component move away from each other along the lateral direction, 2) the second expandable lateral component expands along the lateral direction as respective entireties of the first inferior bone contacting component and the second inferior bone contacting component move away from each other along the lateral direction, and 3) the at least one expandable vertical component expands along the vertical direction as respective entireties of the superior bone contacting member and the inferior bone contacting member move away from each other along the vertical direction, wherein when the implant is in the first insertion configuration, the at least one abutment surface of the superior bone contacting member abuts the at least one abutment surface of the inferior bone contacting member, and when the implant is in the second expanded configuration, the at least one abutment surface of the superior bone contacting member is spaced from the at least one abutment surface of the inferior bone contacting member along the vertical direction, wherein when the implant is in the second expanded configuration, the implant defines 1) a line that extends along the superior bone facing surface from the first outer surface to the first inner surface a first distance in a plane that is oriented in the vertical and lateral directions, wherein the plane is disposed midway between the proximal terminal end and the distal terminal end, 2) a second straight line that extends from the first line at first inner surface to the second inner surface a second distance in the plane, and 3) a third line that extends along the superior bone facing surface from the second straight line at second inner surface to the second outer surface a third distance in the plane, such that a sum of the first and third distances is greater than the second distance, and wherein when the implant is in the second expanded configuration, the implant further defines 1) a fourth line that extends from the third outer surface to the third inner surface a fourth distance in the plane, 2) a fifth straight line that extends from the fourth line at the third inner surface to the fourth inner surface a fourth distance in the plane, and 3) a sixth line that extends from the fifth straight line at the fourth inner surface to the fourth outer surface a sixth distance in the plane, such that a sum of the fourth and sixth distances is greater than the fifth distance.

2. The implant of claim 1, further comprising a cavity defined between the superior bone contacting member and the inferior bone contacting member; and an expansion member insertable in the cavity, the expansion member configured to move the superior bone contacting member with respect to the inferior bone contacting member such that the implant expands along the vertical direction from the first insertion configuration to the second expanded configuration.

3. The implant of claim 1, wherein the implant is expandable from the first insertion configuration to the second expanded configuration without causing the implant to change in length along the longitudinal direction.

4. The implant of claim 3, wherein the length is defined by a distance between the proximal terminal end and the distal terminal end along the longitudinal direction.

5. The implant of claim 1, wherein each of the fourth and sixth lines extend along the inferior bone facing surface.

6. The implant of claim 5, further comprising a plurality of inferior teeth that project out from the inferior bone facing surface.

7. The implant of claim 6, further comprising a plurality of superior teeth that project out from the superior bone facing surface.

8. The implant of claim 1, wherein the first expandable lateral component, the second expandable lateral component, and the at least one expandable vertical component each comprises wire.

9. The implant of claim 8, wherein the wire is arranged as a wire netting.

10. The implant of claim 9, wherein the wire netting comprises a plurality of individual interconnected link members.

11. The implant of claim 1, wherein the superior and inferior bone contacting members include interconnecting projections and bores.

12. The implant of claim 1, wherein the superior bone contacting member, the inferior bone contacting member, and the at least one expandable vertical component is constructed as an integral part via a layer-wise manufacturing process.

13. The implant of claim 1, wherein the at least one expandable vertical component is a first expandable vertical component interconnected between the first superior bone contacting component and the first inferior bone contacting component, the implant further comprises a second expandable vertical component interconnected between the second superior bone contacting component and the second inferior bone contacting component, and the first and second expandable vertical components are expandable along the vertical direction as the implant expands from the first insertion configuration to the second expanded configuration.

14. The implant of claim 1, wherein when the implant is in the first insertion configuration, the implant is elongate along a longitudinal axis that is oriented along the longitudinal direction.

15. The implant of claim 1, further comprising a plurality of superior teeth that project out from the superior bone facing surface.

16. The implant of claim 15, further comprising a plurality of inferior teeth that project out from the inferior bone facing surface.

17. The implant of claim 1, further comprising a plurality of inferior teeth that project out from the inferior bone facing surface.

* * * * *